United States Patent [19]

Bunji et al.

[11] Patent Number: 5,405,828
[45] Date of Patent: Apr. 11, 1995

[54] TETRAHYDROFURAN DERIVATIVE AND HERBICIDE CONTAINING THE SAME AS ACTIVE INGREDIENT

[75] Inventors: Natsume Bunji; Kyomura Nobuo; Suzuki Seiichi, Tokyo; Takahashi Yoji, Tokyo; Jikihara Tetsuo, Tokyo, all of Japan

[73] Assignee: Mitsubishi Kasei Corporation, Tokyo, Japan

[21] Appl. No.: 186,134

[22] Filed: Jan. 25, 1994

Related U.S. Application Data

[62] Division of Ser. No. 979,231, Nov. 20, 1992, Pat. No. 5,324,709.

[30] Foreign Application Priority Data

Dec. 2, 1991 [JP] Japan .................. 3-318210
Oct. 23, 1992 [JP] Japan .................. 4-286273

[51] Int. Cl.⁶ .............. A01N 43/40; A01N 43/08; C07D 405/12; C07D 471/04
[52] U.S. Cl. .................. 504/246; 504/286; 504/294; 546/121; 548/465; 548/517
[58] Field of Search ............ 548/465, 517; 546/121; 504/246, 286, 294

[56] References Cited

U.S. PATENT DOCUMENTS

| | | | |
|---|---|---|---|
| 4,536,209 | 8/1985 | Jikihara et al. | 504/286 |
| 4,806,145 | 2/1989 | Maravetz | 548/262.3 |
| 4,816,063 | 3/1989 | Yamaguchi et al. | 544/235 |
| 4,927,448 | 5/1990 | Yamaguchi et al. | 544/235 |

FOREIGN PATENT DOCUMENTS

| | | |
|---|---|---|
| 0104484 | 4/1984 | European Pat. Off. |
| 0104532 | 4/1984 | European Pat. Off. |
| 0126419 | 11/1984 | European Pat. Off. |
| 0138527 | 4/1985 | European Pat. Off. |
| 0233151 | 8/1987 | European Pat. Off. |
| 0238711 | 9/1987 | European Pat. Off. |
| 0260228 | 3/1988 | European Pat. Off. |
| 0273417 | 7/1988 | European Pat. Off. |
| 0384973 | 9/1990 | European Pat. Off. |
| 0415642 | 3/1991 | European Pat. Off. |

0457714 11/1991 European Pat. Off.

(List continued on next page.)

OTHER PUBLICATIONS

Mitsubishi Chem. Ind. KK, DAJ Abstracts No. 44584 K/19 (1983).

(List continued on next page.)

*Primary Examiner*—Bernard Dentz
*Attorney, Agent, or Firm*—Wenderoth, Lind & Ponack

[57] ABSTRACT

A tetrahydrofuran derivative represented by the following general formula [I]:

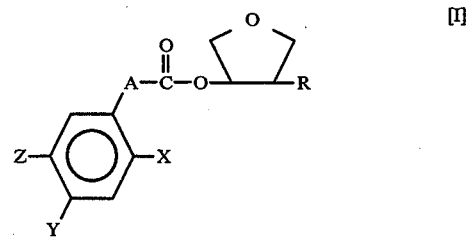

[wherein A represents direct bonding or a group represented by —B—CHR¹— (wherein B represents oxygen atom, sulfur atom or imino group; $R^1$ represents hydrogen atom or an alkyl group); R represents hydrogen atom, halogen atom, hydroxyl group, an alkoxy group, benzyloxy group, an alkylsulfonyloxy group or a group represented by —O—COR² (wherein $R^2$ represents an alkyl group, a haloalkyl group, an alkenyl group, a cycloalkyl group, phenyl group, benzyl group, an alkoxy group, an alkylamino group or a dialkylamino group; X represents halogen atom; Y represents hydrogen atom or halogen atom) and the herbicide containing the same as the effective ingredient. The compounds of the present invention have exceedingly high herbicidal activity, and furthermore, the compounds are superior to the known similar compounds in terms of safety on crops. Thus, the compounds are useful as herbicides.

5 Claims, No Drawings

FOREIGN PATENT DOCUMENTS 3827221 2/1990 Germany.
2071100 9/1981 United Kingdom.
2127410 4/1984 United Kingdom.
WO86/02642 5/1986 WIPO.
WO88/10254 12/1988 WIPO.

OTHER PUBLICATIONS

Mitsubishi Chem. Ind. KK, DAJ Abstracts No. 31342 E/16 (1982).
Mitsubishi Chem. Ind. KK, DAJ Abstracts No. 83–841268/50 (1983).
Sumitomo Chemical KK, DAJ Abstracts No. 84–279285/45 (Aug. 1989).
Mitsubishi Chem. Ind. KK, DAJ Abstracts No. 86–004858/01 (Jun. 1986).
Mitsubishi Chem. Ind. KK, DAJ Abstracts No. 140810/22 (Jun. 1986).
Nippon Soda KK, DAJ Abstracts No. 88–095027/14 (Aug. 1988).
Kumai Chem. Ind. KK, DAJ Abstracts No. 87–040749/06 (Oct. 1987).
Kumai Chem. Ind. KK, DAJ Abstracts No. 89–274534/38 (Sep. 1989).
Nissan Chem. Ind. KK, DAJ Abstracts 89–062692/09 (Jun. 1989).
Mitsubishi Chem. Ind. KK, DAJ Abstracts 86–096634/15 (Jul. 1986).
Mitsubish Chem. Ind. KK, DAJ Abstracts 85–181193/30 (Apr. 1985).
Nihon Noyaku KK, DAJ Abstracts 84–034252/06 (Feb. 1984).
Nihon Noyaku KK, DAJ Abstracts No. 46944 D/26 (Mar. 1981).
Mitsubishi Chem. Ind. KK, DAJ Abstracts 85–232488/38 (Apr. 1985).

TETRAHYDROFURAN DERIVATIVE AND HERBICIDE CONTAINING THE SAME AS ACTIVE INGREDIENT

This application is a division of application Ser. No. 07/979,231, filed Nov. 20, 1992, now U.S. Pat. No. 5,324,709.

FIELD OF THE INVENTION

The present invention relates to a novel tetrahydrofuran derivative and a herbicide containing the same as the active ingredient.

BACKGROUND OF THE INVENTION

As herbicides, proposition has been made of heterocyclic compounds substituted with phenyl groups having certain types of substituents, such as N-(substituted phenyl)-3, 4, 5, 6-tetrahydrophthalimides, 3-(substituted phenyl)-1, 5-tetramethylenehydantoins, 4-(substituted phenyl)-1, 2-tetramethyleneurazoles, 9-(substituted phenylimino)-8-thia-1, 6-diazabicyclo[4.3. 0]nonan-7-ones, 3-(substituted phenyl)-1, 3, 4-oxadiazolin-2-ones and the like. However, these compounds generally have low selectivity between weeds and crops, so they cannot satisfy both of herbicidal activity and safety for crops. Thus, they are presently put to practical use only in a limited field.

Although a great number of substituted-phenyl heterocyclic compounds with herbicidal activity have been proposed as has been described above, few of them have both the safety for significant crops and sufficient herbicidal activity, so that herbicides provided with the two properties have been expected. In case of taking account of environmental influence as well, a herbicide with less dose for application is preferable.

The present inventors have made intensive investigations on the problems described above, and have found that certain specific compounds having a tetrahydrofuran ring have characteristic properties such that the compounds have high herbicidal activity and nevertheless do not show almost any influence on a great number of significant crops. Thus, they have achieved the present invention.

That is, the gist of the present invention resides in novel tetrahydrofuran derivatives, represented by the following general formula [I]:

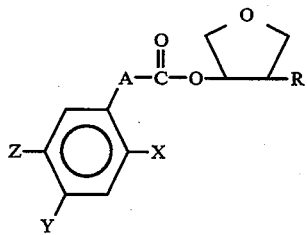

{wherein A represents direct bonding or a group represented by —B—CHR¹— (wherein B represents oxygen atom, sulfur atom or imino group; $R^1$ represents hydrogen atom or an alkyl group of $C_1$–$C_4$);

R represents hydrogen atom, halogen atom, hydroxyl group, an alkoxy group of $C_1$–$C_4$, benzyloxy group, an alkylsulfonyloxy group of $C_1$–$C_3$ or a group represented by —O—COR² (wherein $R^2$ represents an alkyl group of $C_1$–$C_5$, a haloalkyl group of $C_1$–$C_3$, an alkenyl group of $C_2$–$C_5$, a cycloalkyl group of $C_3$–$C_6$, phenyl group, benzyl group, an alkoxy group of $C_1$–$C_4$, an alkylamino group of $C_1$–$C_4$ or a dialkylamino group of $C_2$–$C_6$);

X represents halogen atom;

Y represents hydrogen atom or halogen atom;

Z is a group represented by

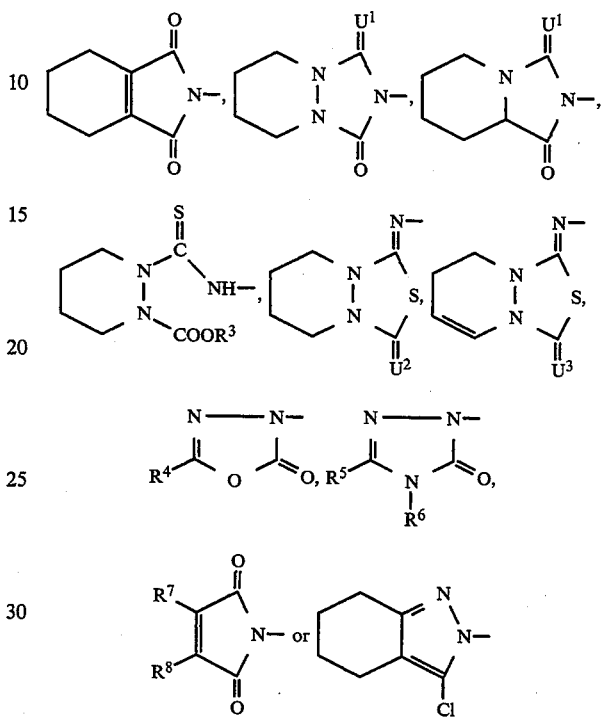

(wherein $U^1$, $U^2$ and $U^3$ independently represent oxygen atom or sulfur atom; $R^3$, $R^4$, $R^5$, $R^6$, $R^7$ and $R^8$ independently represent an alkyl group of $C_1$–$C_4$)}; and a herbicide containing the same as the active ingredient.

The compounds of the present invention will now be explained in details.

In accordance with the present invention, the tetrahydrofuran derivatives to be used as a herbicide is represented by the above general formula [I].

In the above general formula [I], A represents direct bonding or a group represented by —B—CHR¹— (wherein B represents O, S or NH; $R^1$ represents hydrogen atom or an alkyl group of $C_1$–$C_4$ such as methyl group, ethyl group, n-propyl group, isopropyl group, n-butyl group and the like).

R represents hydrogen, atom; halogen atom such as fluorine atom, chlorine atom, bromine atom and the like; hydroxyl group; an alkoxy group of $C_1$–$C_4$ such as methoxy group, ethoxy group, n-propoxy group, isopropoxy group, n-butoxy group, isobutoxy group, sec-butoxy group, t-butoxy group and the like; benzyloxy group; an alkylsulfonyloxy group of $C_1$–$C_3$ such as methylsulfonyloxy group, ethylsulfonyloxy group, n-propylsulfonyloxy group, isopropylsulfonyloxy group, and the like; or a group represented by —O—COR² (wherein $R^2$ represents an alkyl group of $C_1$–$C_5$ such as methyl group, ethyl group, n-propyl group, isopropyl group, n-butyl group, isobutyl group, sec-butyl group, t-butyl group, n-pentyl group, isopentyl group, neopentyl group, t-pentyl group, 1-methylbutyl group, 2-methylbutyl group, 1-ethylpropyl group, 1,2-dimethylpropyl group and the like; a haloalkyl group of $C_1$–$C_3$ such as chloromethyl group, bromomethyl group, 2- chloroethyl group, 2-bromoethyl group, 3-chloropropyl group, 3-bromopropy group, difluoromethyl group, dichloromethyl group, trifluoromethyl group, trichloromethyl group, 2, 2, 2-trifluoroethyl group and the like; an alkenyl group of $C_2$–$C_5$ such as vinyl group, allyl group, 1-propenyl group, 1-methylvinyl group, 2-butenyl group, 3-butenyl group, 1-methylallyl group, 2-methylallyl group, 2-pentenyl group, 3-pentenyl group, 4-pentenyl group, 3-methyl-2-butenyl group, 2-methyl-3-butenyl group, 4-pentenyl group, 3-methyl-2-butenyl group, 2-methyl-3-butenyl group, 3-methyl-3-butenyl group, 1-methyl-2-butenyl group, 1-methyl-3-butenyl group and the like; a cycloalkyl group of $C_3$–$C_6$ such as cyclopropyl group, cyclobutyl group, cyclopentyl group, cyclohexyl group and the like; phenyl group; benzyl group; an alkoxy group of $C_1$–$C_4$ such as those described above as the R; an alkylamino group of $C_1$–$C_4$ such as methylamino group, ethylamino group, n-propylamino group, isopropylamino group, n-butylamino group, isobutylamino group, sec-butylamino group, t-butylamino group and the like; or a dialkylamino group of $C_2$–$C_6$ such as dimethylamino group, diethylamino group, di-n-propylamino group, diisopropylamino group, methylethylamino group, methyl-n-propylamino group and the like.

X represents halogen atom such as those as described above as the R; Y represents hydrogen atom or halogen atom such as those described above as the R. Z is a group represented by

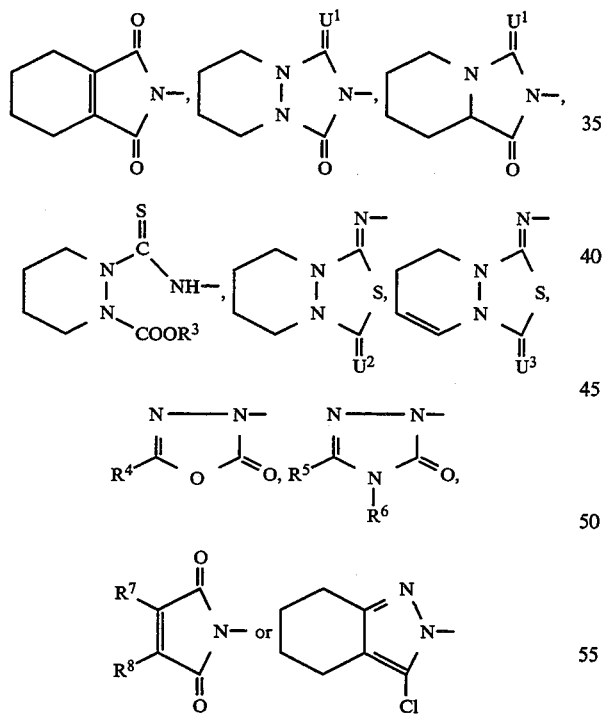

(wherein $U^1$, $U^2$ and $U^3$ independently represent oxygen atom or sulfur atom; $R^3$, $R^4$, $R^5$, $R^6$, $R^7$ and $R^8$ independently represent an alkyl group of $C_1$–$C_4$ such as methyl group, ethyl group, n-propyl group, isopropyl group, n-butyl group, isobutyl group, sec-butyl group, t-butyl group and the like).

The compounds of the present invention are preferably ones wherein R represents hydrogen atom, hydroxyl group, benzyloxy group, an alkylsulfonyloxy group of $C_1$–$C_3$ or a group represented by —O—COR$^2$ (wherein $R^2$ represents an alkyl group of $C_1$–$C_5$, a haloalkyl group of $C_1$–$C_3$, an alkenyl group of $C_2$–$C_5$, a cycloalkyl group of $C_3$–$C_6$, phenyl group, and an alkoxy group of $C_1$–$C_4$ [in particular, R more preferably represents hydrogen atom, hydroxyl group or an alkylsulfonyloxy group of $C_1$–$C_3$, or a group represented by —O—COR$^2$ group (wherein $R^2$ represents an alkyl group of $C_1$–$C_5$, an alkenyl group of $C_2$–$C_5$, a cycloalkyl group of $C_3$–$C_6$, a phenyl group or an alkoxy group of $C_1$–$C_3$)]; and Z represents a group represented by

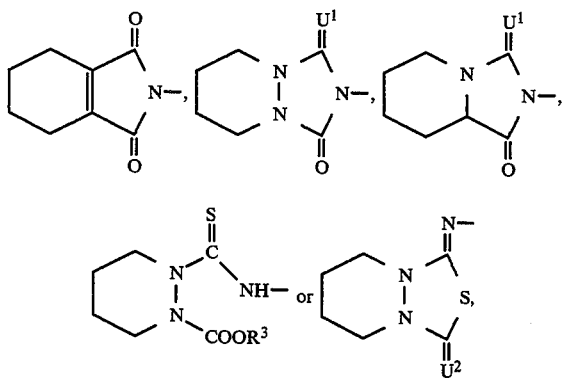

(wherein $U^1$ and $U^2$ independently represent oxygen atom or sulfur atom; $R^3$ represents an alkyl group of $C_1$–$C_3$). (As Z, the one representing

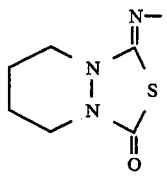

is preferable.)

More preferable compounds are ones wherein A represents —SCH$_2$—; R represents a group represented by —O—COR$^2$ (wherein $R^2$ represents an alkyl group of $C_1$–$C_5$); X and Y represent halogen atom; and Z represents

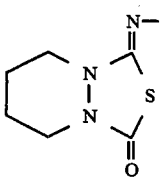

Particularly preferable compounds include 9-(5-(4-acetoxytetrahydrofuran-3-yloxycarbonylmethylthio)-4-chloro-2-fluorophenylimino)-8-thia-1, 6-diazabicyclo[4.3.0]nonan7-one (Compound No. 26 in Table 1 described below) shown in Example 11 described below.

The method for producing the compounds of the present invention will now be explained below.

The compounds of the present invention represented by the above general formula [I], can be synthesized, for example, by the following reaction scheme.

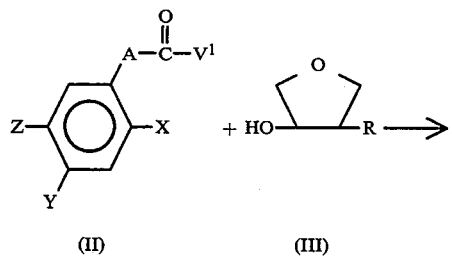 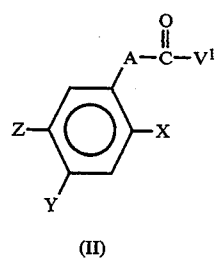

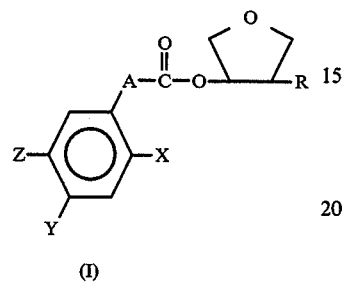

(In the above reaction scheme, $V^1$ represents halogen atom such as chlorine atom, bromine atom and the like; A, R, X, Y, and Z independently represent the same meanings as described above.)

The above reaction is carried out without a solvent or in a solvent in the presence or absence of a base, generally in a temperature range of 0° to 100 °C. Appropriate solvent if used includes aromatic hydrocarbons such as benzene, toluene, xylene and the like; halogenated hydrocarbons Such as dichloromethane, chloroform, 1,2-dichloroethane and the like; ethers such as diethyl ether, tetrahydrofuran, dioxane and the like; esters such as methyl acetate, ethyl acetate and the like; ketones such as acetone, methyl ethyl ketone and the like; polar solvents such as N, N-dimethylformamide, N-methylpyrrolidone, dimethyl sulfoxide, acetonitrile and the like. The bases to be used include triethylamine, pyridine, picoline, N, N-dimethylaniline, sodium hydrogencarbonate, potassium hydrogen carbonate, sodium carbonate, potassium carbonate, sodium hydroxide, potassium hydroxide, sodium methylate, sodium ethylate, sodium hydride and the like.

The starting material compound [II] can be produced by reacting the corresponding carboxylic acid XI] with a halogenating agent such as thionyl chloride, phosphorous trichloride, phosphorous tribromide and the like. The compound [XI] is described in each gazette of Japanese Patent Laid-open Nos. 149267/1982, 189178/1983, 225070/1983, 109578/1985, 149571/1985, and 76487/1986, European Patent Publication Nos. 49508, 77938 and 126419.

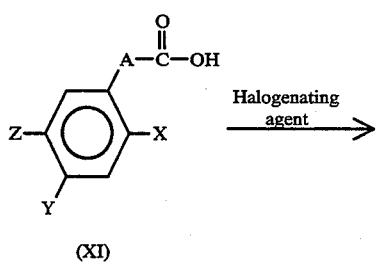

(In the above scheme, A, X, Y, Z, and $V^1$ independently represent the same meanings as described above.)

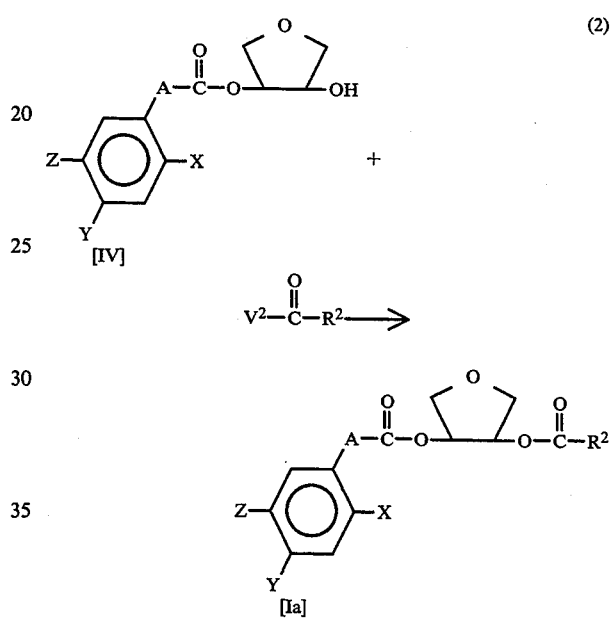

(In the above reaction scheme, $V^2$ represents halogen atom such as chlorine atom, bromine atom and the like; A, $R^2$, X, Y, and Z independently represent the same meanings as described above.)

The above reaction is carried out without a solvent or in a solvent in the presence of a base, generally in a temperature range of 0° to 100 °C. Appropriate solvent if used includes those described in (1). The bases to be used include those described in (1).

The starting material [IV] is a compound wherein R is hydroxyl group in the compound [I] of the present invention, and can be produced by the methods shown in the process (1) described above, and the processes (3), (4), (5), (6) and (7) described below.

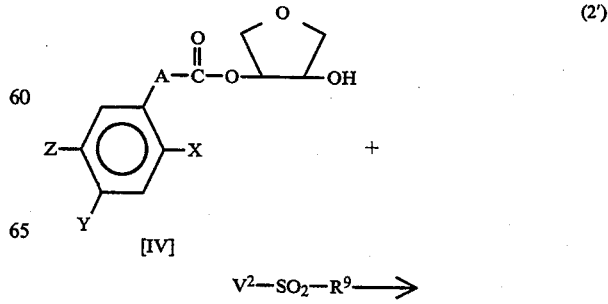

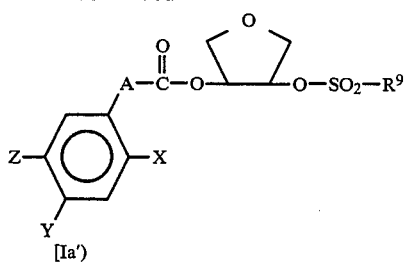

[Ia']

(In the above reaction scheme, A, X, Y, Z and $V^2$ independently represent the same meanings as described above; and $R^9$ represents an alkyl group of $C_1$–$C_3$ such as methyl group, ethyl group, n-propyl group, isopropyl group.)

The above reaction is carried out without a solvent or in a solvent in the presence of a base, generally in a temperature range of 0° to 100 °C. Appropriate solvent if used includes those described in (1). The bases to be used include those described in (1).

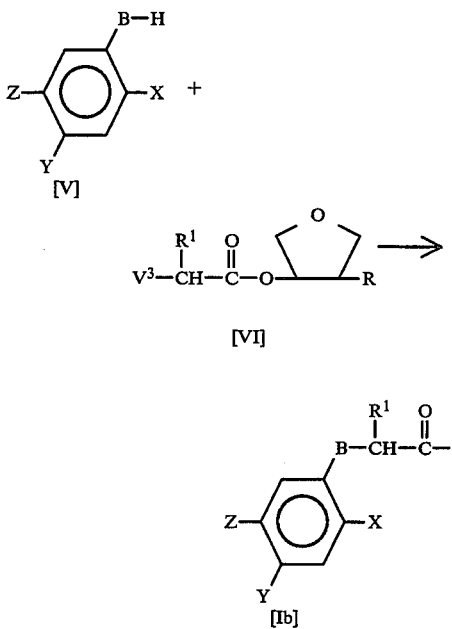

[V]

[VI]

[Ib]

(In the above reaction scheme, $V^3$ represents halogen atom such as chlorine atom, bromine atom, iodine atom; B, R, $R^1$, X, Y and Z independently represent the same meanings as described above.)

The above reaction is carried out without a solvent or in a solvent in the presence of a base, generally in a temperature range of room temperature to 200° C. Appropriate solvent if used includes those described in (1), and besides, the bases to be used include those described in (1).

In case $V^3$ means Cl or Br, iodide such as sodium iodide, potassium iodide, and the like may be added to acclerate the reaction.

The starting material IV] is described in each gazette of Japanese Patent Laid-open Nos. 53662/1981, 83672/1983, 189178/1983, 172491/1984, 109578/1985, 149571/1985, 233075/1985, 40261/1986, and 76487/1986, European Patent Publication No. 77938 and United Kingdom Patent Publication No. 2127410.

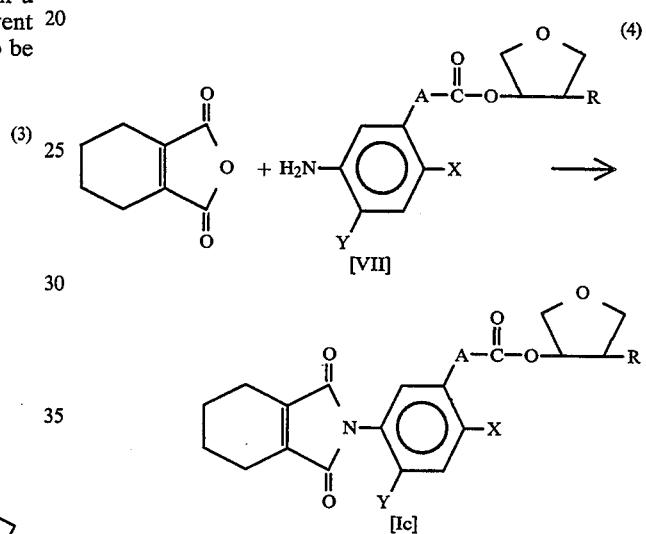

[VII]

[Ic]

(In the above reaction scheme, A, R, X, and Y independently represent the same meanings as described above.)

The above reaction is carried out without a solvent or in a solvent under heating, generally in a temperature range of 50° to 200 °C. Appropriate solvent if used includes water; and polar solvents including carboxylic acids such as acetic acid, alcohols such as methanol, ethanol, propanol, butanol, etc.; and the like, in addition to these described in (1).

The starting material [VII] can be produced, for example, by the method shown in the following scheme.

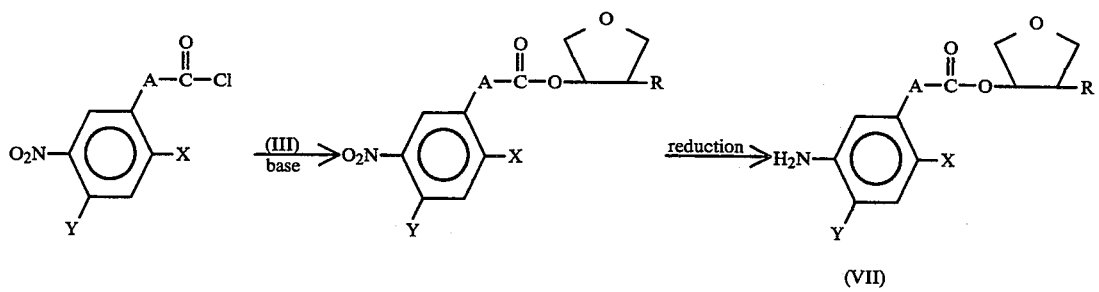

(VII)

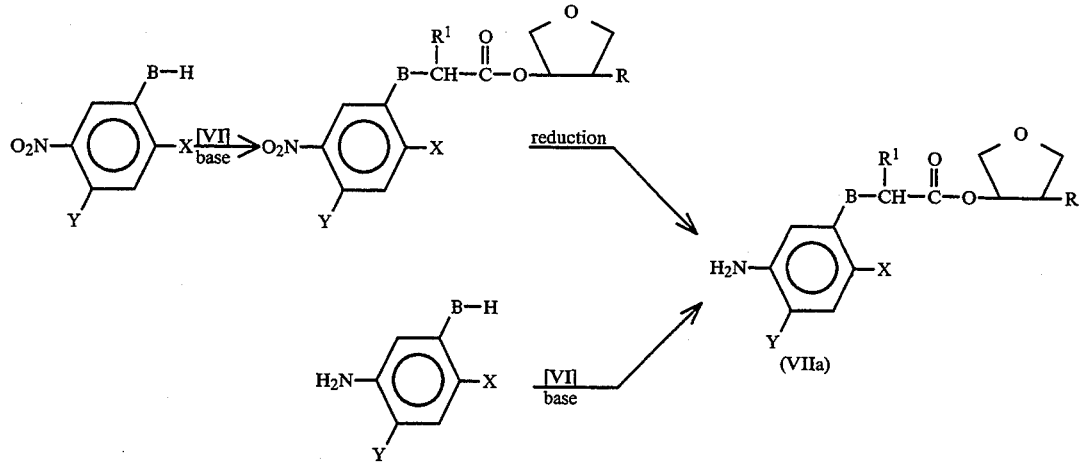

(In the above scheme, A, B, R, $R^1$, X and Y independently represent the same meanings as described above.)

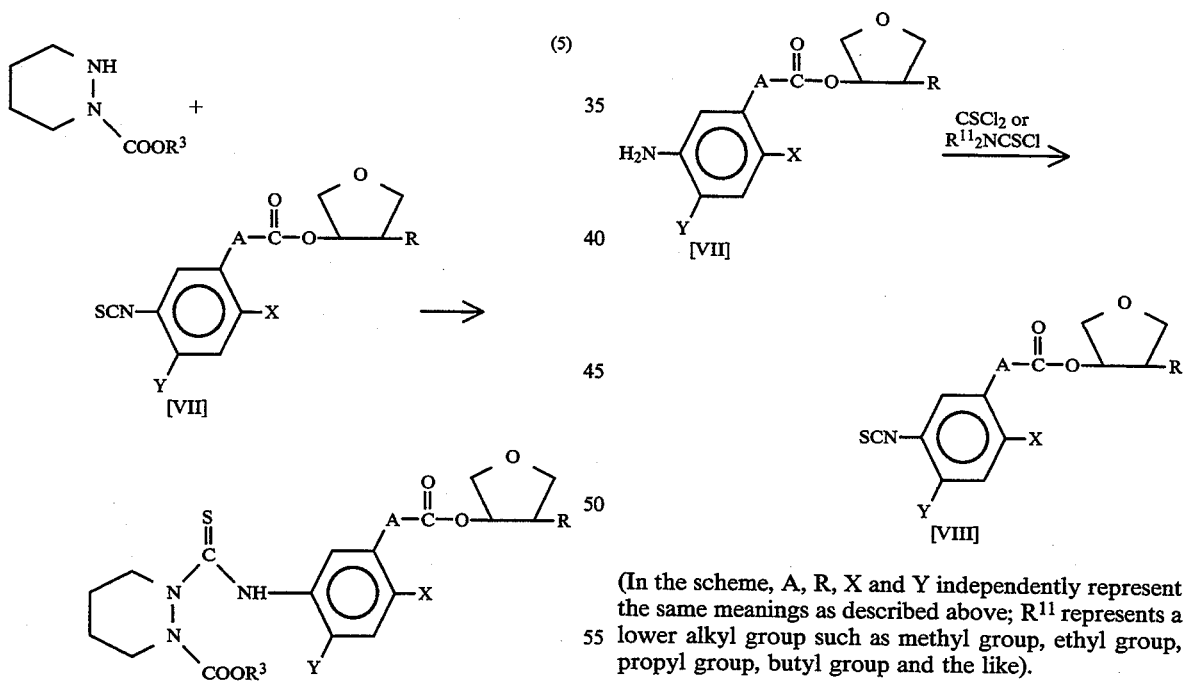

(In the reaction scheme, A, R, X, Y, and $R^3$ independently represent the same meaning as described above.)

The above reaction is carried out without a solvent or in a solvent, generally in a temperature range of 0° to 100 °C. Appropriate solvent if used includes those described in (1).

The starting material [VIII] can be produced by reacting the compound [VII] described hereinabove with thiophosgene or N, N-dialkylthiocarbamoyl chloride.

(In the scheme, A, R, X and Y independently represent the same meanings as described above; $R^{11}$ represents a lower alkyl group such as methyl group, ethyl group, propyl group, butyl group and the like).

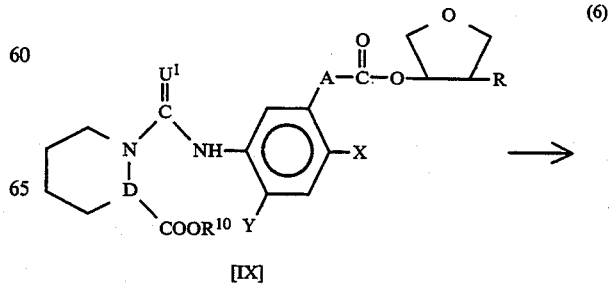

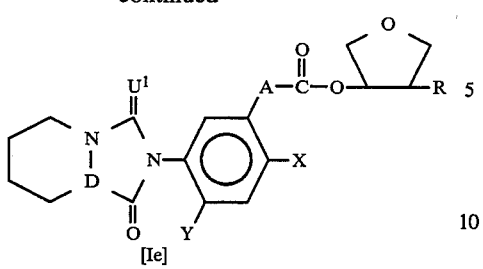

(In the above reaction scheme, $R^{10}$ represents hydrogen atom or an alkyl group of $C_1$-$C_4$ such as methyl group, ethyl group, propyl group, butyl group and the like; D represents —N— or —CH—; A, R, X, Y and $U^1$ independently represent the same meanings as described above.)

The above reaction is carried out without a solvent or in a solvent in the presence or absence of a base, generally in a temperature range of room temperature to 200 ° C. Appropriate solvent if used includes polar solvents such as alcohols such as methanol, ethanol, propanol and the like; water and the like, in addition to those described in (1). The bases to be used include those described in (1).

The starting material [IX] can be produced from the compound [VII] described above, for example, by the method shown in the following scheme. In the scheme, phosgene or trichloromethyl chloroformate is used for the preparation of isocyanate ($U^1$=O) in the reaction of the first stage. And, thiophosgene or N, N-dialkylthiocarbamoyl chloride is used for the preparation of isothiocyanate ($U^1$=S).

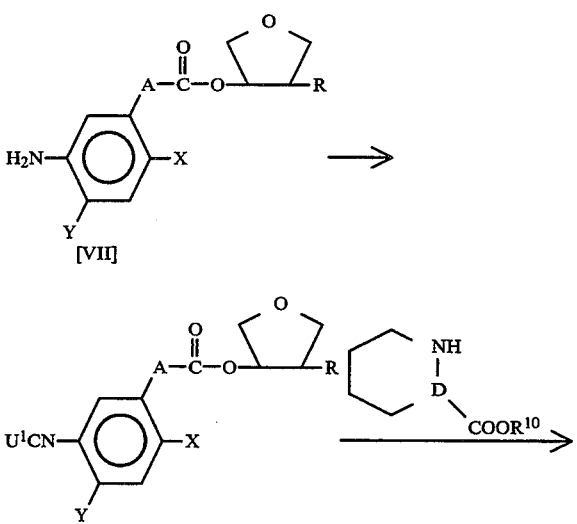

(In the scheme, A, R, X, Y, $U^1$, D and $R^{10}$ independently represent the same meanings as described above.)

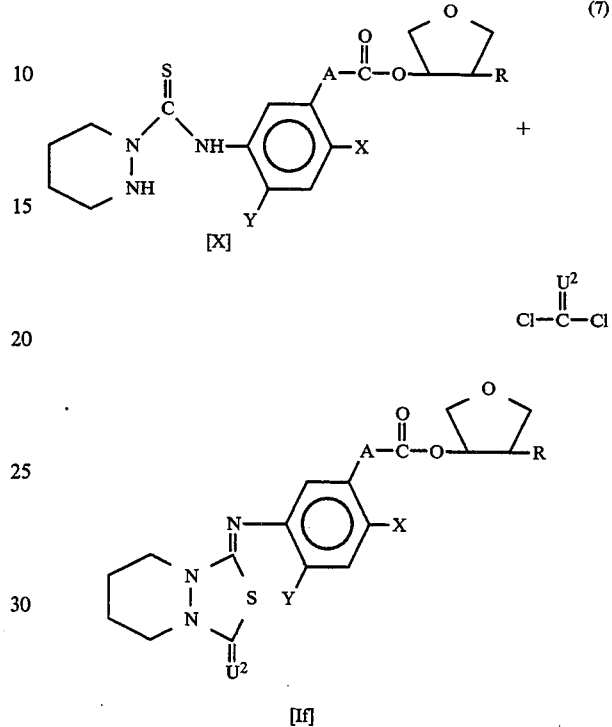

(In the above reaction scheme, A, R, X, Y and $U^2$ independently represent the same meanings as described above.)

The above reaction is carried out by reacting phosgene ($U^2$=O) or thiophosgene ($U^2$=S) without a solvent or in a solvent in the presence of a base, generally in a temperature range of −10° to 100 ° C. In case of $U^2$=O, trichloromethyl chloroformate can be used instead of phosgene. Appropriate solvent if used includes those descried in (1). The bases to be used include those described in (1).

The starting material [X] can be produced by reacting the compound [VIII] described above with hexahydropyridazine.

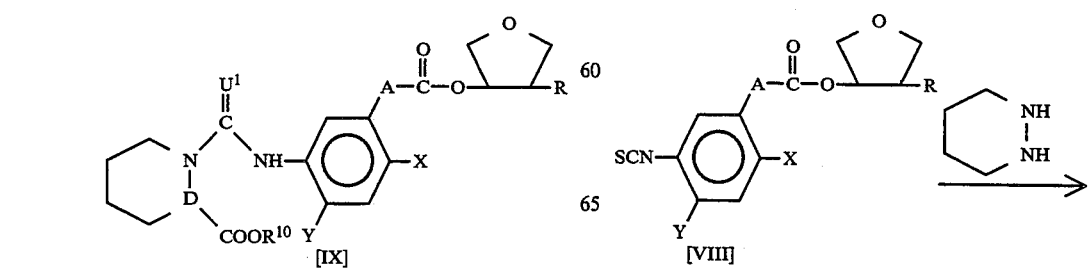

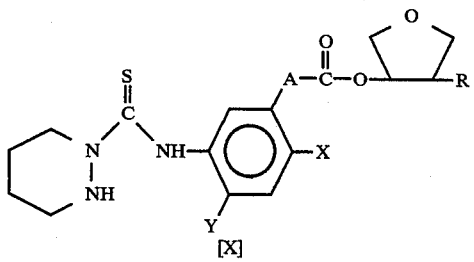

[X]

(In the above scheme, A, R, X and Y independently represent the same meanings as described above.)

The compounds of the present invention thus obtained have isomers such as optical isomers, diastereomer and the like. The present invention includes all of them. The compounds of the present invention can be used as a herbicides singly as in the form of each of the isomers thereof or as an appropriate mixture of the isomers.

In using the compounds of the present invention as a herbicide, the technical product may be applied as it is. However, the compound is generally used in the form of wettable powder, granule, emulsifiable concentrate, flowable and the like by using appropriate auxiliaries. Example of such auxiliaries include solid carrier such as kaolin, bentonite, talc, diamatoceous earth, white carbon, carbohydrate and the like; solvents including water, alcohols (methanol, ethanol, propanol, butanol, ethylene glycol and the like), ketones (acetone, methyl ethyl ketone, cyclohexanone and the like), ethers (diethyl ether, dioxane, cellosolves and the like), aliphatic hydrocarbons (kerosin, kerosene, and the like), aromatic hydrocarbons (benzene, toluene, xylene, solvent naphtha, methylnaphthalene and the like), halogenated hydrocarbon (dichloroethane, trichlorobenzene, carbon tetrachloride and the like), amides (dimethylformamide and the like), esters (ethyl acetate, butyl acetate, fatty acid glycerin esters and the like), nitriles (acetonitrile and the like); surfactant including nonionic surfactant (polyoxyethylene alkylallyl ether, polyoxyethylene sorbitan monolaurate and the like), cationic surfactant (alkyl dimethylbenzylammonium chloride, alkylpyridium chloride and the like), anionic surfactant (alkylbenzene sulfonate, lignin sulfonate, higher alcohol sulfate and the like), amphoteric surfactant (alkyl dimethyl betaine, dodecylaminoethyl glycine and the like), and the like. These solid carriers, solvents, and surfactants are individually used in a mixture of one or two or more thereof, depending on needs.

The dose for application of the compounds of the present invention varies depending on the structure of the compound, the subjective weeds, the application time, the application method, the soil properties and the like, but the dose as the active ingredient thereof is generally in a range of 5–2000 g, preferably 10–1000 g per ha.

The subjective weeds of the compounds of the present invention are, for example, *Chenopodium album, Chenopodium serotinum, Polygonum lapathifolium, Polygonum persicaria, Amaranthus lividus, Amaranthus viridis, Stellaria media, Lamium amplexicaule, Digitaria adscendens, Eleusine indica, Echinochloa Crus-galli, Setaria viridis*, and the like in upland fields; in paddy fields, for example, *Rotala indica, Lindernia pyridaria, Monochoria vaginalis, Dopatrium junceum, Elatine triandra, Alisma canadiculatum, Echinochloa oryzicola, Cyperus difformis*, and the like. Furthermore, the compounds of the present invention exhibits high herbicidal activity on those weeds which have been hard to be controlled by known herbicides, including, for example, *Abutilon theophrasti, Xanthium strumarium, Ipomoea indica, Datura Stramonium, Brassica juncea, Galium aparine, Viola tricolor, Matricaria matricarioides, Bidens pilosa,* and the like in upland fields; in paddy fields, for example, *Sagittaria pygmaea, Sagitaria trifolia, Scirpus juncoides, Cyperus serotinus*, and the like. The compounds of the present invention show herbicidal activity against the weeds described above through the soil application in pre-emergent stage and the foliar application in post-emergent stage. The compound of the present invention also have less influence on crops such as corn, wheat, barley, sorgho, rice, soybean, potato and the like through soil application in pre-emergent stage and foliar application in post-emergent stage, and can be used as a selective herbicide.

The herbicide containing the compound of the present invention as the active ingredient can be mixed and applied with other pesticides such as, for example, insecticides, fungicides, plant growth regulators, or fertilizers. By mixing and applying with other herbicides, the herbicidal activity of the compound can be stabilized. The herbicides which can preferably be mixed with, include the following, for example:

Pyrazole herbicides; 4-(2, 4-dichlorobenzoyl)-1, 3-dimethylpyrazol-5-yl p-toluenesulfonate, 4-(2, 4-dichlorobenzoyl)-1, 3-dimethyl-5-phenacyloxypyrazole, 4-(2, 4-dichloro-3-methylbenzoyl)-1,3-dimethyl-5-(4-methylphenacyloxy)pyrazole, 4-(2, 4-dichlorobenzoyl)-1-methyl-5-phenacyloxypyrazole, and the like;

Sulfonylurea herbicides; methyl 2-(4, 6-dimethoxypyridin-2-ylcarbamoylaminosulfonylmethyl)benzoate, ethyl 5-(4, 6-dimethoxypyridin-2-ylcarbamoylaminosulfonyl)-1-methylpyrazole-4-carboxylate, 2-chloro-N-(4-methoxy-6-methyl-1, 3, 5-triazin-2-ylaminocarbonyl)benzene sulfonamide, methyl 2-(4-methoxy-6-methyl-1, 3, 5-triazin-2-ylcarbamoylaminosulfonyl)benzoate, methyl 2-(4, 6-dimethylpyridin-2-ylcarbamoylaminosulfonyl)benzoate, ethyl 2-(4-chloro-6-methoxypyridin-2-ylcarbamoylaminosulfonyl)benzoate, and the like;

Phenoxy herbicides; (2, 4-dichlorophenoxy)acetate and the derivatives thereof, (4-chloro-2-methylphenoxy)acetate and the derivatives thereof, 4-(4-chloro-2-methylphenoxy)butylate and the derivatives thereof, S-ethyl 4-chloro-2-methylphenoxy)thioacetate, 2-(2-naphthoxy)propione anilide, 2-(2, 4-dichloro-3-methylphenoxy)propione anilide, butyl 2-[4-(5-trifluoromethyl-2-pyridyloxy)phenoxy]propionate;

Haloacetanilide herbicides; 2-chloro-2', 6'-diethyl-N-methoxymethylacetanilide, 2-chloro-2',6'-diethyl-N-butoxymethylacetanilide, 2-chloro-2'-ethyl-6'-methyt-N-(2-methoxy-1-methylethyl)acetanilide, 2-chloro2',6'-diethyl-N-propoxyethylacetanilide, ethyl N-chloroacetyl-N-(2, 6-diethylphenyl)aminoacetate, 2-chloro-2',6'-dimethyl-N-(3-methoxy-2-tenylmethyl)acetanilide and the like;

Amide herbicides; 3',4'-dichloropropionanilide, 2',3'-dichloro-4-ethoxymethoxybenzanilide, 2-bromo-3,3-dimethyl-N-(α,α-dimethylbenzyl)butylic acid amide, 2-benzothiazol-2-yloxy-N-methylacetanilide, 2',4'-difluoro-2-(3-trifluoromethylphenoxy)nicotinanilide, 2,6-dimethoxy-N(3-(1-ethyl-1-methylpropyl)isoxazol-5-yl)benzamide, and the like;

Carbamate herbicides; S-(4-chlorobenzyl) N,N-diethylthiocarbamate, S-ethyl N,N-hexamethylenethiocarbamate, S-isopropyl N,N-hexamethylenethiocarbamate, S-benzyl N-ethyl-N-(1,2-dimethylpropyl)thiocarbamate, S-(1-methyl-1-phenetyl) piperidine 1-carbothioate, O-(3-t-butylphenyl) N-(6-methoxypyridin-2-yl)-N-methylthiocarbamate, S-ethyl N,N-di(n-propylthiol carbamate), S-ethyl N,N-diisobutylthiocarbamate, isopropyl N-(3-chlorophenyl)carbamate, 3-(methoxycarbonylamino)phenyl N-(3-methylphenyl)carbamate, S-(2,3-dichloroallyl) N,N-diisopropylthiocarbamate, S-(2, 3, 3-trichloroallyl) N,N-diisopropylthiocarbamate, methyl N-(4-aminobenzenesulfonyl)carbamate and the like;

Urea herbicides; 1-(α,α-dimethylbenzyl)-3-(4-methylphenyl)urea, 3-(benzothiazol-2-yl)-1,3-dimethylurea, 3-(3,4-dichlorophenyl)-1-methoxy-1-methylurea, 3-(3,4-dichlorophenyl)-1,1-dimethylurea, 3-[4-(4-methylphenetyloxy)phenyl]-1-methoxy-1-methylurea, 3-(4-isopropylphenyl)-1,1-dimethylurea, 1-(2-substituted benzyl)-3-(α,α-dimethylbenzyl)ureas and the like;

Diphenyl ether herbicides; 2, 4, 6-trichloro-4'-nitrodiphenyl ether, 2,4-dichloro-3'-methoxy-4'-nitrodiphenyl ether, methyl 5-(2, 4-dichlorophenoxy)-2-nitrobenzoate, 3-[5-(2-chloro-4-trifluoromethylphenoxy)2-nitrophenoxy]tetrahydrofuran, 5-(2-chloro-4-trifluoromethylphenoxy)-2-nitrobenzoate and the salts thereof, 2-chloro-3'-ethoxy-4'-nitro-4-trifluoromethyldiphenyl ether, 1-(ethoxycarbonyl)ethyl 5-(2-chloro-4-trifluoromethylphenoxy)-2-nitrobenzoate, 5-(2-chloro-4-trifluoromethylphenoxy)-N-(methylsulfonyl)-2-nitrobenzamide, methyl 5-(2-chloro-4-trifluoromethylphenoxy)-2-nitroacetophenone oxime-O-acetate, 3-amino-2-chloro-4-nitrodiphenyl ether and the like;

Triazine herbicides; 2-chloro-4-ethylamino-6-isopropylamino-1, 3, 5-triazine, 2, 4-bis(ethylamino)-6-methylthio-1,3,5-triazine, 2-ethylamino-4-(1,2-dimethylpropylamino)-6-methylthio-1,3,5-triazine, 2,4-bis-(isopropylamino)-6-methylthio-1,3,5-triazine, 4-amino-6-t-butyl-3-methylthio-1,2,4-triazine-5(4H)-one, 4-amino-6-t-butyl-3-ethylthio-1,2,4-triazine-5(4H)-one, 2-chloro-4,6-bis(ethylamino)-1,3,5-triazine, 2-(2-chloro-4-ethylamino-1,3,5-triazin-6-ylamino)-2-methylpropionitrile and the like;

Dinitroaniline herbicides; 2,6-dinitro-N,N-dipropyl-4-(trifluoromethyl)aniline, N-(1-ethylpropyl)3,4-dimethyl-2,6-dinitroaniline, 3,5-dinitro-$N^4$, $N^4$-dipropylsulfanilide and the like;

Nitrile herbicides; 4-hydroxy-3,5-diiodobenzonitrile, 3,5-dibromo-4-hydroxybenzonitrile, 2,6-dichlorobenzonitrile and the like;

Phosphorous-containing herbicides; O-ethyl O-(5-methyl-2-nitrophenyl) N-sec-butylphosphoroamidate, S-(2-(benzenesulfonylamino)ethyl) O,O-diisopropyl phosphorodithioate, S-((2-methylpiperidin-1-yl)carbonylmethyl) O,O-dipropyl phosphorodithioate, N-(phosphonomethyl)glycine, ammonium (DL-homoalanin-4-yl(methyl)phosphonate, sodium 4-(hydroxy(methyl)phosphinoyy)-L-homoalanyl-L-alanyl-L-alanate, and the like;

Quarternary-ammonium salts herbicides; 1,1'-ethylene-2,2'-bipyridium dibromide, 1,1'-dimethyl-4,4'-bipyridium dichloride and the like;

Other herbicides; 3,6-dichloro-2-methoxybenzoate, 3,7-dichloroquinoline-8-carboxylic acid, pentachlorophenol, 2-sec-butyl-4,6-dinitrophenol, 2-amino-3-chloro-1,4-naphthoquinone, 1,2-dihydropyridazine-3,6-dione, 3-(2methylphenoxy)pyridazine, 3-isopropyl-1H-2,1,3-benzothiadiazin-4(3H)-one 2,2-dioxide, 2,2-dichloropropionic acid, 2,2,3,3-tetrafluoropropionic acid, methyl 6-(4-isopropyl-4-methyl-5-oxo-2-imidazolin-2-yl)-3(4)-methylbenzoate, 2-(4-isopropyl-4-methyl-5-oxo-2-imidazolin-2-yl)nicotinic acid and the salts thereof, 2-(4-isopropyl-4-methyl-5-oxo-2-imidazolin-2-yl)quinoline-3-carboxylic acid, 5-ethyl-2-(4-isopropyl-4-methyl-5-oxo-2-imidazolin-2-yl)nicotinic acid, 1-methyl-4-(1-methylethyl)-2-((2-methylphenyl)methoxy)-7-oxabicyclo[2.2.1]heptane, 1-(3-methylphenyl)-5-phenyl-1H-1,2,4-triazole-3-carboxamide, 2-(N-ethoxybutylimidyl)-5-(2-ethylthiopropyl)-3-hydroxy-2-cyclohexen-1-one, 2-(3,5-dichlorophenyl)-2-(2,2,2-trichloroethyl)oxirane, N-[4-chlorobenzyloxy)phenyl]-3,4,5,6-tetrahydrophthalimide, N-(4-chloro-2-fluoro-5-propargyloxyphenyl)-3,4,5,6-tetrahydrophthalimide, 3-(2,4-dichloro-5-isopropoxyphenyl)-5-t-butyl-1,3,4-oxadiazole-2(3H)-one, 4-methoxy-3,3'-dimethylbenzophenone, 2-ethoxy-2,3-dihydro-3,3-dimethyl-5-benzofuranyl methanesulfonate, 1-methyl-3-phenyl-5-(3-trifluoromethylphenyl)pyridine-4(1H)-one, 2-(2-chlorophenyl)methyl-4,4-dimethyl-3-isoxazolidinone, (E), (E)-2-(1-(3-chloropropen-2-yloxyimino)butyl)-5-(2-ethylthiopropyl)-3-hydroxy-2-cyclohexen-1-one, 2-(1-ethoxyiminopropyl)-3-hydroxy-5-dimethyl-2-dichlorohexen-1-one and the like.

These can be mixed in plurality for use.

The present invention will now be explained in details with reference with examples, but the invention is not limited to the following examples, unless departing from the scope thereof.

Example 1

N-(3-(4-Acetoxytetrahydrofuran-3-yloxycarbonyl)-4-chlorophenyl)-3,4,5,6-tetrahydrophthalimide A mixture of 12.2 g of N-(3-carboxy-4-chlorophenyl)-3,4,5,6-tetrahydrophthalimide and 20 ml of thionyl chloride was refluxed under stirring for 2 hours. Distilling off excess thionyl chloride, the resulting acid chloride was dissolved in 40 ml of ethyl acetate. In 80 ml of ethyl acetate were dissolved 6.4 g of 3-acetoxy-4-hydroxytetrahydrofuran and 4.9 g of triethylamine, to which was added a solution of the acid chloride in ethyl acetate under stirring. After stirring at room temperature for 3 hours, the reaction mixture was washed with water and subsequently with aqueous saturated sodium chloride solution, and dried over anhydrous magnesium sulfate. After distilling off the solvent, the residue was purified by chromatography on a silica gel column (eluted with ethyl acetate/hexane =½), to obtain 11.7 g of a compound described in Table 1 (No. 1) (67%).

Example 2

N-(5-(4-Acetoxytetrahydrofuran-3-yloxycarbonylmethoxy)-4-chloro-2-fluorophenyl)-3,4,5,6-tetrahydrophthalimide In 15 ml of benzene were dissolved 0.66 g of N-(4-chloro-2-fluoro-5-(4-hydroxytetrahydrofuran-3-yloxycarbonylmethoxy)phenyl)-3,4,5,6tetrahydrophthalimide and 0.20 g of triethylamine, followed by dropwise addition of a solution of 0.14 g of acetyl chloride in benzene. After stirring at room temperature for 4 hours, the reaction mixture was washed with water and subsequently with aqueous saturated sodium chloride solution, and 'dried over anhydrous magnesium sulfate. After distilling off the solvent, the residue was purified by chromatography on a silica gel column (eluted with ethyl acetate/hexane=⅔), to obtain 0.55 g of a compound described in Table 1 (No.3) (76%).

Example 3

9-(4-Chloro-5-(4-(chloroacetoxy)tetrahydrofuran-3-yloxycarbonylmethylthio)-2-fluorophenylimino)-8-thia-1,6-diazabicyclo[4.3.0]nonan-7-one In 25 ml of dichloromethane were dissolved 1.19 g of 9-(4-chloro-2-fluoro-5-(4-hydroxytetrahydrofuran-3-yloxycarbonylmethylthio)phenylimino)- 8-thia-1,6diazabicyclo[4.3.0]nonan-7-one and 0.24 g of pyridine, followed by dropwise addition of a solution of 0.34 g of chloroacetyl chloride in dichloromethane. After stirring at room temperature overnight, the reaction mixture was washed with water, and subsequently with aqueous saturated sodium chloride solution, and dried over anhydrous magnesium sulfate. After distilling off the solvent, the residue was purified by chromatography on a silica gel column (eluted with ethyl acetate/hexane =⅔), to obtain 1.02 g of a compound described in Table 1 (No. 32) (74%).

Example 4

9-(4-Chloro-2-fluoro-5-(4-methylsulfonyloxy)tetrahydrofuran-3-yloxycarbonylmethylthio)phenylimino-8-thia-1,6diazabicyclo[4.3.0]nonan-7-one In 15 ml of pyridine was dissolved 1.43 g of 9-(4-chloro-2-fluoro-5-(4-hydroxytetrahydrofuran-3-yloxycarbonylmethylthio)phenylimino)-8-thia-1,6-diazabicyclo[4.3.0]nonan-7-one, followed by dropwise addition of 0.69 g of methanesulfonyl chloride under stirring while in ice cooling and subsequent stirring overnight at room temperature. After distilling off pyridine under reduced pressure, the residue was extracted with toluene, which was then washed sequentially with water, dilute hydrochloric acid, aqueous saturated sodium hydrogencarbonate solution, and aqueous saturated sodium chloride solution, and dried over anhydrous magnesium sulfate. After distilling off the solvent, the residue was purified by chromatography on a silica gel column (eluted with ethyl acetate/hexane =3/2), to obtain 1.40 g of a compound described in Table 1 (No. 25) (84%).

Example 5

9-(4-Chloro-5-(4-(ethoxycarbonyloxy)tetrahydrofuran-3-yloxycarbonylmethylthio)-2-fluorophenylimino-8-thia-1,6diazabicyclo[4.3.0]nonan-7-one In 15 ml of pyridine was dissolved 1.43 g of 9-(4-chloro-2-fluoro-5-(4-hydroxytetrahydrofuran-3-yloxycarbonylmethylthio)phenylimino)-8-thia-1,6diazabicyclo[4.3.0]nonan-7-one, followed by dropwise addition of 0.65 g of ethyl chloroformate under stirring while in ice cooling and subsequent stirring overnight at room temperature. After distilling off pyridine under reduced pressure, the residue was extracted with ethyl acetate, which was then washed with water and subsequently with aqueous saturated sodium chloride solution, and dried over anhydrous magnesium sulfate. After distilling off the solvent, the residue was purified by chromatography on a silica gel column (eluted with ethyl acetate/hexane=⅔), to obtain 1.38 g of a compound described in Table 1 (No. 36) (84%).

Example 6

N-(5-(4-Acetoxytetrahydrofuran-3-yloxycarbonylmethylthio)-4-chloro-2-fluorophenyl)3,4,5,6-tetrahydrophthalimide A mixture of 14.0 g of N-(4-chloro-2-fluoro-5-mercaptophenyl)-3,4,5,6-tetrahydrophthalimide, 11.0 g of 4-acetoxytetrahydrofuran-3-yl chloroacetate, 7.46 g of potassium carbonate, 1.5 g of potassium iodide and 150 ml of acetone was refluxed under stirring for 5 hours. After cooling, the salt was filtered off, and the residue was purified by chromatography on a silica gel column (eluted with ethyl acetate/hexane=⅔), to obtain 14.5 g of a compound described in Table 1 (No. 6) (65%).

Example 7

N-(5-(1-(4-Acetoxytetrahydrofuran-3-yloxycarbonyl)ethylamino)-4-chloro-2-fluorophenyl)-3,4,5,6-tetrahydrophthalimide A mixture of 8.84 g of N-(5-amino-4-chloro-2-fluorophenyl)-3,4,5,6-tetrahydrophthalimide, 12.6 g of 4-acetoxytetrahydrofuran-3-yl 2-bromopropionate, 3.02 g of sodium hydrogencarbonate and 3 ml of xylene was heated under stirring at 150° to 160 ° C. for 4 hours. Adding ethyl acetate to the reaction mixture while it remained warm, the resulting mixture was washed with water, subsequently with aqueous saturated sodium chloride solution, and dried over anhydrous magnesium sulfate. After distilling off the solvent, the residue was purified by chromatography on a silica gel column (development solvent: ethyl acetate/hexane=½), to obtain 4.88 g of a compound described in Table 1 (No. 10) (33%).

Example 8

1-(5-(4-Acetoxytetrahydrofuran-3-yloxycarbonylmethoxy)-4-chloro-2-fluorophenylaminothiocarbonyl)-2-(ethoxycarbonyl)hexahydroxypridazine Seventy-five milliliters of water were cooled in an ice-cold bath, followed by addition of 2.3 g of thiophosgene and subsequent dropwise addition of a solution of 5.2 g of 5-(4-acetoxytetrahydrofuran-3-yloxycarbonylmethoxy)-4-chloro-2-fluoroaniline in 150 ml of chloroform. After stirring at room temperature for 2 hours, the organic layer was washed with water, subsequently with aqueous saturated sodium chloride solution, and dried over anhydrous magnesium sulfate. After distilling off the solvent, the resulting isothiocyanate was dissolved in 75 ml of benzene, followed by addition of 2.4 g of ethyl 1,2-tetramethylenecarbazate, which was then refluxed under stirring for 1 hour. After cooling, the reaction mixture was washed with water, subsequently with aqueous saturated sodium chloride solution, and dried over anhydrous magnesium sulfate. After distilling off the solvent, the residue was purified by chromatography on a silica gel column (eluted with ethyl acetate/chloroform =1/6), to obtain 5.3 g of a compound (No. 17) described in Table 1 (64%).

Example 9

4-(5-(4-Acetoxytetrahydrofuran-3-yloxycarbonylmethoxy)-4-chloro-2-fluorophenyl)1,2-tetramethylene-3-thiourazole In 20 ml of toluene were dissolved 2.19 g of 1-(5-(4-acetoxytetrahydrofuran-3-yloxycarbonylmethoxy)-4-chloro-2-fluorophenylaminothiocarbonyl)-2-(ethoxycarbonyl)hexahydropyridazine and 0.49 g of triethylamine, and refluxed under stirring for 8 hours. After distilling off the solvent from the reaction mixture, the residue was purified by chromatography on a silica gel column (eluted with ethyl acetate/hexane=3/2), to obtain 1.34 g of a compound (No. 14) described in Table 1 (67%).

Example 10

3-(5-(4-Acetoxytetrahydrofuran-3-yloxycarbonylmethoxy)-4-chloro-2-fluorophenyl)-1,5-tetramethylene-2-thiohydantoin A mixture of the isothiocyanate produced from 1.39 g of 5-(4-acetoxytetrahydrofuran-3-yloxycarbonylmethoxy)-4-chloro-2-fluoroaniline in the same fashion as in Example 8, 0.62 g of pipecolic acid and 20 ml of ethanol was refluxed under stirring for 4 hours. To the resulting mixture was poured water, which was then extracted with ethyl acetate, washed with aqueous saturated sodium chloride solution, and dried over anhydrous magnesium sulfate. After distilling off the solvent, the residue was purified by chromatography on a silica gel column (eluted with ethyl acetate/hexane =1/1), to obtain 1.05 g of a compound (No. 12) described in Table 1 (52%).

Example 11

9-(5-(4-Acetoxytetrahydrofuran-3-yloxycarbonylmethylthio)-4-chloro-2-fluorophenylimino)-8-thia-1,6-diazabicyclo[4.3.0]nonan-7-one In 15 ml of dichloromethane was dissolved 1.48 g of 1-(5-(4-acetoxytetrahydrofuran-3-yloxycarbonylmethylthio)-4-chloro-2-fluorophenylaminothiocarbonyl)-hexahydropyridazine, followed by addition of 0.59 g of pyridine, which was then cooled in an ice-cold bath. Under stirring, 3.3 g of a 26.8% solution of phosgene in toluene was added dropwise, and after addition was completed, the resulting product was stirred at room temperature for 3 hours. The reaction mixture was washed with water, subsequently with aqueous saturated sodium chloride solution, and dried over magnesium sulfate. After distilling off the solvent, the residue was purified by chromatography on a silica gel column (eluted with ethyl acetate/hexane=1/1), to obtain 1.20 g of a compound (No. 26) described in Table 1 (77%).

Example 12

9-(5-(4-Acetoxytetrahydrofuran-3-yloxycarbonylmethoxy)-4-chloro-2-fluorophenylimino)-8-thia-1,6diazabicyclo[4.3.0]nonan-7-thione In 15 ml of dichloromethane was dissolved 1.43 g of 1-(5-(4-acetoxytetrahydrofuran-3-yloxycarbonylmethoxy)-4-chloro-2-fluorophenylaminothiocarbonyl)hexahydropyridazine, followed by addition of 0.59 g of pyridine, which was then cooled in an ice-cold bath. Under stirring, a solution of 0.52 g of thiophosgene in dichloromethane was added dropwise, and after addition was completed, the resulting mixture was stirred at room temperature for 3 hours. The reaction mixture was washed with water, subsequently with aqueous saturated sodium chloride solution, and dried over magnesium sulfate. After distilling off the solvent the residue was purified by chromatography on a silica gel column (eluted with ethyl acetate/hexane=$\frac{2}{3}$), to obtain 1.12 g of a compound (No. 42) described in Table 1 (72%).

The other compounds described in Table 1 can be synthesized according to any of the methods described in the Examples 1 to 12. All of the structures of the resulting compounds were confirmed by IR, NMR spectra and the like. The physical properties and $^1$H-NMR spectra of the compounds described in Table 1 are shown in Table 2.

TABLE 1

| Compound No. | Z | X | Y | A | R | Synthesis (Example No.) |
|---|---|---|---|---|---|---|
| 1 | cyclohexene-fused imide (N-linked, with two C=O) | —Cl | —H | Direct bonding | —OCCH$_3$ (O=) | 1 |
| 2 | " | —Cl | —F | —OCH$_2$— | —OH | 6 |
| 3 | " | —Cl | —F | —OCH$_2$— | —OCCH$_3$ (O=) | 2 |
| 4 | " | —Cl | —F | —SCH$_2$— | —H | 6 |
| 5 | " | —Cl | —F | —SCH$_2$— | —OH | " |
| 6 | " | —Cl | —F | —SCH$_2$— | —OCCH$_3$ (O=) | " |
| 7 | " | —Cl | —F | —SCH(CH$_3$)— | —OCCH$_3$ (O=) | " |
| 8 | " | —Cl | —F | —SCH(C$_2$H$_5$)— | —OCCH$_3$ (O=) | " |
| 9 | " | —Cl | —F | —NHCH$_2$— | —OCCH$_3$ (O=) | 7 |

TABLE 1-continued

| Compound No. | Z | X | Y | A | R | Synthesis (Example No.) |
|---|---|---|---|---|---|---|
| 10 | " | —Cl | —F | —NHCH(CH$_3$)— | —OCOCH$_3$ | " |
| 11 | 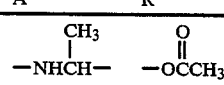 | —Cl | —F | —NHCH$_2$— | —OCOCH$_3$ | 7 |
| 12 |  | —Cl | —F | —OCH$_2$— | —OCOCH$_3$ | 10 |
| 13 | 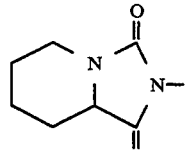 | —Cl | —H | Direct bonding | —OCOCH$_3$ | 9 |
| 14 | " | —Cl | —F | —OCH$_2$— | —OCOCH$_3$ | " |
| 15 | " | —Cl | —F | —SCH$_2$— | —OCOCH$_3$ | 9 |
| 16 |  | Cl | —H | Direct bonding | —OCOCH$_3$ | 8 |
| 17 | " | —Cl | —F | —OCH$_2$— | —OCOCH$_3$ | " |
| 18 | 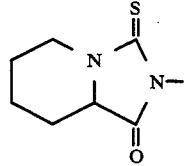 | —Cl | —H | Direct bonding | —OCOCH$_3$ | 11 |
| 19 | " | —Cl | —H | —SCH$_2$— | —OCOCH$_3$ | " |
| 20 | " | —Cl | —F | —OCH$_2$— | —OH | " |
| 21 | " | —Cl | —F | —OCH$_2$— | —OCOCH$_3$ | " |
| 22 | " | —Cl | —F | —SCH$_2$— | —H | " |
| 23 | " | —Cl | —F | —SCH$_2$— | —OH | " |
| 24 | " | —Cl | —F | —SCH$_2$— | —OCH$_2$C$_6$H$_5$ | " |
| 25 | " | —Cl | —F | —SCH$_2$— | —OSO$_2$CH$_3$ | 4 |

TABLE 1-continued

| Compound No. | Z | X | Y | A | R | Synthesis (Example No.) |
|---|---|---|---|---|---|---|
| 26 | " | —Cl | —F | —SCH$_2$— | —OC(=O)CH$_3$ | 11 |
| 27 | " | —Cl | —F | —SCH$_2$— | —OC(=O)C$_2$H$_5$ | " |
| 28 | (bicyclic structure) | —Cl | —F | —SCH$_2$— | —OC(=O)-n-C$_3$H$_7$ | 11 |
| 29 | " | —Cl | —F | —SCH$_2$— | —OC(=O)-i-C$_3$H$_7$ | " |
| 30 | " | —Cl | —F | —SCH$_2$— | —OC(=O)-n-C$_4$H$_9$ | " |
| 31 | " | —Cl | —F | —SCH$_2$— | —OC(=O)-i-C$_4$H$_9$ | " |
| 32 | " | —Cl | —F | —SCH$_2$— | —OC(=O)CH$_2$Cl | 3 |
| 33 | " | —Cl | —F | —SCH$_2$— | —OC(=O)CH$_2$CH=CH$_2$ | 11 |
| 34 | " | —Cl | —F | —SCH$_2$— | —OC(=O)-cyclohexyl | 3 |
| 35 | " | —Cl | —F | —SCH$_2$— | —OC(=O)-phenyl | " |
| 36 | " | —Cl | —F | —SCH$_2$— | —OC(=O)OC$_2$H$_5$ | 5 |
| 37 | " | —Cl | —F | —SCH(CH$_3$)— | —OC(=O)CH$_3$ | 11 |
| 38 | (bicyclic structure) | —Cl | —F | —SCH(C$_2$H$_5$)— | —OC(=O)CH$_3$ | 11 |
| 39 | " | —Cl | —F | —NHCH$_2$— | —OC(=O)CH$_3$ | " |
| 40 | " | —Cl | —F | —NHCH(CH$_3$)— | —OC(=O)CH$_3$ | " |
| 41 | " | —Cl | —Cl | —SCH$_2$— | —OC(=O)CH$_3$ | " |

TABLE 1-continued

| Compound No. | Z | X | Y | A | R | Synthesis (Example No.) |
|---|---|---|---|---|---|---|
| 42 | 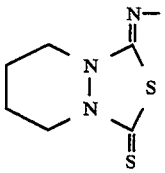 | —Cl | —F | —OCH₂— | $-OCCH_3$ with =O | 12 |
| 43 | " | —Cl | —F | —SCH₂— | $-OCCH_3$ with =O | " |

TABLE 2

| Compound No. | Melting point or refractive index | ¹H-NMR (δ, CDCl₃) |
|---|---|---|
| 1 | | 7.93(1H,d), 7.57–7.48(2H, m), 5.58(1H, q), 5.44(1H, q), 4.23–4.12(2H, m), 4.01(1H, dd), 3.86(1H, dd), 2.47–2.40(4H, m), 2.09(3H, s), 1.87–1.80(4H, m) |
| 2 | mp 111~113.5° C. | 7.27(1H, d), 6.80(1H, d), 5.11(1H, q), 4.72(2H, s), 4.34(1H, q), 4.09–3.34 (4H, m), 2.69(1H, d), 2.39(4H, m), 1.81(4H, m) |
| 3 | | 7.32(1H, d), 6.86(1H, d), 5.41(2H, m), 4.70(2H, s) 4.19–3.70(4H, m), 2.04 (3H, s), 2.44(4H, m), 1.83(4H, m) |
| 4 | mp 116~117° C. | 7.40(1H, d), 7.33(1H, d), 5.32–5.27(1H, m), 3.88–3.73(4H, m), 3.64(2H, s), 2.47–2.40(4H, m), 2.21–2.08(1H, m), 1.98–1.88(1H, m), 1.87–1.79(4H, m) |
| 5 | mp 153~154° C. | 7.41(1H, d), 7.33(1H, d), 5.14(1H, q), 4.44(1H, q), 4.03(1H, dd), 3.93(1H, dd), 3.78(1H, dd), 3.72(2H, AB), 3.59(1H, dd), 2.47–2.38(4H, m), 1.87–1.78(4H, m) |
| 6 | | 7.41(1H, d), 7.33(1H, d), 5.37–5.27(2H, m), 4.06–4.00(2H, m), 3.79–3.72 (2H, m), 3.67(2H, s), 2.47–2.40(4H, m), 2.04(3H, s), 1.86–1.79(4H, m) |
| 7 | | 7.49, 7.48(Total 1H, d), 7.36, 7.34(Total 1H, d), 5.33–5.25(2H, m), 4.10–3.87(3H, m), 3.79–3.58(2H, m), 2.47–2.40(4H, m), 2.05, 2.04(Total 3H, s), 1.87–1.80(4H, s), 1.54(3H, d) |
| 8 | | 7.48(1H, d), 7.35, 7.33(Total 1H, d), 5.33–5.25(2H, m), 4.10–3.74(2H, m), 3.78–3.55(3H, m), 2.47–2.40(4H, m), 2.04, 2.03(Total 3H, s), 2.02–1.79(6H, m), 1.08, 1.08(Total 3H, t) |
| 9 | | 7.22(1H, d), 6.38(1H,d), 5.45(1H, q), 5.33(1H, q), 4.84(1H, bd), 4.13–4.06 (2H, m), 3.96(2H, s), 3.88–3.77(2H, m), 2.46–2.39(4H, m), 2.04(3H, s), 1.86–1.79(4H, m) |
| 10 | | 7.21(1H, d), 6.42, 6.41(Total 1H, d), 5.45–5.28(2H, m), 4.73, 4.65(Total 1H, bd), 4.20–4.02(3H, m), 3.90–3.71(2H, m), 2.46–2.39(4H, m), 2.01, 1.97(Total 3H, s), 1.85–1.79(4H, m), 1.54(3H, d) |
| 11 | | 7.23(1H, d), 6.44(1H, d), 5.46(1H, q), 5.34(1H, q), 4.86(1H, bs), 4.28–3.78 (8H, m), 2.98–2.87(1H, m), 2.34–2.26(1H, m), 2.10–2.02(1H, m), 2.05(3H, s) 1.84–1.76(1H, m), 1.62–1.41(3H, m) |
| 12 | | 7.32, 7.32(Total 1H, d) 6.95–6.87(1H, m), 5.49–5.41(1H, m), 5.37–5.30(1H, m) 4.92–4.84(1H, m), 4.78–4.63(2H, m), 4.14–4.00(3H, m), 3.88–3.77(2H, m), 3.16–3.04(1H, m), 2.38–2.30(1H, m) 2.14–2.04(1H, m) 2.07, 2.06, 2.05, 2.05 (Total 3H, s), 1.96–1.84(1H, m), 1.72–1.48(3H, m) |
| 13 | mp 157.5~158.5° C. | 8.04–8.02(1H, m), 7.62–7.60(2H, m), 5.61–5.56(1H, m), 5.44(1H, q), 4.22–3.99(5H, m), 3.86(1H, dd), 3.77–3.70(2H, m), 2.07(3H, s), 2.06–1.94(4H, m) |
| 14 | | 7.35(1H, d), 6.98(1H, d), 5.45(1H, q), 5.33(1H, q), 4.71(2H, AB), 4.12–3.99 (4H, m), 3.88–3.68(4H, m), 2.06(3H, s), 2.04–1.94(4H, m) |
| 15 | | 7.57, 7.55(Total 1H, d), 7.37(1H, d), 5.37–5.27(2H, m), 4.14–3.93(4H, m), 3.83–3.64(6H, m), 2.06, 2.05(Total 3H, s), 2.05–1.93(4H, m) |
| 16 | | 8.38(1H, bs), 7.95–7.93(1H, m), 7.72(1H, dd), 7.45(1H, d), 5.60–5.40(3H, m), 4.34–3.84(7H, m), 3.14–3.00(2H, m), 2.07(3H, s), 1.94–1.70(4H, m), 1.33 (3H, t) |
| 17 | | 8.46, 8.45(Total 1H, bs), 8.18, 8.15(Total 1H, d), 7.17(1H, d), 5.50–5.42(2H, m), 5.33 (1H, q), 4.75(2H, s), 4.33–4.06(5H, m), 3.92–3.77(2H, m), 3.11–2.99(2H, m), 2.08, 2.07(Total 3H, s), 1.90–1.70(4H, m), 1.30(3H, t) |
| 18 | | 7.43(1H, d), 7.41(1H, d), 7.03(1H, dd), 5.60–5.54(1H, m), 5.44(1H, q), 4.23–4.11(2H, m), 4.01(1H, dd), 3.87(1H, dd), 3.80–3.71(4H, m), 2.05(3H, s), 1.98–1.79(4H, m) |
| 19 | mp 130.5–131.5° C. | 7.32(1H, d), 6.98(1H, d), 6.75(1H, dd), 5.39–5.27(2H, m), 4.09–4.03(2H, m), 3.84–3.70(6H, m), 3.71(2H, s), 2.02(3H, s), 1.96–1.78(4H, m) |
| 20 | mp 139~140.5° C. | 7.18(1H, d), 6.55(1H, d), 5.28–5.23(1H, m), 4.74(2H, s), 4.54–4.46(1H, m), 4.09(1H, dd), 3.99(1H, dd), 3.87(1H, dd), 3.81–3.64(5H, m), 2.17(1H, bd), 1.97–1.78(4H, m) |
| 21 | | 7.18(1H, d), 6.54(1H, d), 5.46(1H, q), 5.33(1H, q), 4.67(2H, AB), 4.13–4.05 (2H, m), 3.88–3.71(6H, m), 2.06(3H, s), 1.97–1.78(4H, m) |
| 22 | mp 92~94° C. | 7.20(1H, d), 7.11(1H, d), 5.33–5.28(1H, m), 3.92–3.71(8H, m), 3.62(2H, s), 2.22–2.09(1H, m), 2.00–1.79(5H, m) |
| 23 | | 7.21(1H, d), 7.12(1H, d), 5.18–5.12(1H, m), 4.48–4.41(1H, m), 4.04(1H, dd), 3.96(1H, dd), 3.82–3.64(6H, m), 3.71(2H, s), 2.18(1H, bs), 1.97–1.79(4H, m) |
| 24 | | 7.37–7.25(5H, m), 7.17(1H, d), 7.10(1H, d), 5.35–5.30(1H, m), 4.52(2H, AB), |

TABLE 2-continued

| Compound No. | Melting point or refractive index | $^1$H-NMR ($\delta$, CDCl$_3$) |
|---|---|---|
| 25 | | 4.18–3.67(9H, m), 3.69(2H, AB), 1.93–1.75(4H, m) |
| | | 7.20(1H, d), 7.12(1H, d), 5.30(1H, q), 5.22–5.17(1H, m), 4.13–3.95(3H, m), 3.83–3.70(5H, m), 3.71(2H, s), 3.05(3H, s), 1.97–1.79(4H, m) |
| 26 | mp 106.5~108° C. | 7.20(1H, d), 7.12(1H, d), 5.37–5.27(2H, m), 4.09–4.02(2H, m), 3.83–3.72 (2H, m), 3.65(2H, s), 2.04(3H, s), 1.97–1.79(4H, m) |
| 27 | | 7.20(1H, d), 7.12(1H, d), 5.38–5.28(2H, m), 4.10–4.02(2H, m), 3.83–3.71 (6H, m), 3.64(2H, s), 2.32(2H, q), 1.98–1.79(4H, m), 1.12(3H, t) |
| 28 | | 7.20(1H, d), 7.12(1H, d), 5.38–5.28(2H, m), 4.10–4.02(2H, m), 3.82–3.72 (6H, m), 3.64(2H, s), 2.27(2H, t), 1.97–1.79(4H, m), 1.69–1.56(2H, m), 0.93(3H, t) |
| 29 | nd 23.0° C. 1.5899 | 7.20(1H, d), 7.12(1H, d), 5.38–5.26(2H, m), 4.11–4.03(2H, m), 3.82–3.71 (6H, m), 3.63(2H, AB), 2.54(1H, sep), 1.97–1.79(4H, m), 1.16(3H, d), 1.15(3H, d) |
| 30 | | 7.20(1H, d), 7.12(1H, d), 5.37–5.28(2H, m), 4.10–4.02(2H, m), 3.82–3.7 (6H, m), 3.64(2H, s), 2.29(2H, t), 1.97–1.79(4H, m), 1.63–1.53(2H, m), 1.39–1.27(2H, m), 0.90(3H, t) |
| 31 | | 7.20(1H, d), 7.12(1H, d), 5.37–5.28(2H, m), 4.10–4.02(2H, m), 3.82–3.71 (6H, m), 3.63(2H, s), 2.19–2.16(2H, m), 2.13–2.00(1H, m), 1.97–1.79 (4H, m), 0.94(6H, d) |
| 32 | | 7.21(1H, d), 7.11(1H, d), 5.43–5.33(2H, m), 4.12–4.04(2H, m), 4.07(2H, AB), 3.86–3.72(6H, m), 3.65(2H, s), 1.97–1.79(4H, m) |
| 33 | nd 23.5° C. 1.5994 | 7.20(1H, d), 7.11(1H, d), 5.96–5.81(1H, m), 5.38–5.29(2H, m), 5.22–5.13 (2H, m), 4.10–4.02(2H, m), 3.83–3.71(6H, m), 3.09(2H, d), 1.98–1.79(4H, m) |
| 34 | | 7.20(1H, d), 7.12(1H, d), 5.37–5.26(2H, m), 4.10–4.02(2H, m), 3.82–3.72 (6H, m), 3.63(2H, s), 2.35–2.24(1H, m), 1.97–1.57(9H, m), 1.48–1.16(5H, m) |
| 35 | | 8.02–7.98(2H, m), 7.61–7.55(1H, m), 7.47–7.40(2H, m), 7.10(1H, d), 7.06 (1H, d), 5.56–5.44(2H, m), 4.24–4.10(2H, m), 3.98–3.70(6H, m), 3.59(2H, s), 1.96–1.78(4H, m) |
| 36 | | 7.20(1H, d), 7.13(1H, d), 5.34(1H, q), 5.21(1H, q), 4.20(2H, q), 4.12–4.04 (2H, m), 3.89–3.82(6H, m), 3.65(2H, AB), 1.97–1.79(4H, m), 1.31(3H, t) |
| 37 | | 7.24–7.18(2H, m), 5.34–5.25(2H, m), 4.10–3.96(2H, m), 3.90–3.63(7H, m), 2.06, 2.05(Total 3H, s), 1.52, 1.51(Total 3H, d) |
| 38 | | 7.23–7.17(2H, m), 5.34–5.25(2H, m), 4.11–3.97(2H, m), 3.83–3.61(7H, m), 2.04, 2.04(Total 3H, s), 2.01–1.78(6H, m), 1.07, 1.07(Total 3H, t) |
| 39 | | 7.10(1H, d), 6.13(1H, d), 5.44(1H, q), 5.34(1H, q), 4.74(1H, bs), 4.13–4.06 (2H, m), 3.95(2H, bs), 3.88–3.70(6H, m), 2.05(3H, s), 1.97–1.78(4H, m) |
| 40 | | 7.09(1H, d), 6.18, 6.15(Total 1H, d), 5.44–5.28(2H, m), 4.63, 4.55(Total 1H, bd), 4.17–4.04(3H, m), 3.90–3.70(6H, m), 2.03, 1.99(Total 3H, s), 1.97–1.77(4H, m), 1.54(3H, d) |
| 41 | | 7.45(1H, s), 7.00(1H, s), 5.38–5.27(2H, m), 4.09–4.02(2H, m), 3.84–3.72 (6H, m), 3.68(2H, s), 2.03(3H, s), 1.98–1.79(4H, m) |
| 42 | | 7.18(1H, d), 6.52(1H, d), 5.47(1H, q), 5.34(1H, q), 4.67(2H, AB), 4.20–4.05 (4H, m), 3.90–3.78(4H, m), 2.06(3H, s), 2.04–1.90(4H, m) |
| 43 | | 7.20(1H, d), 7.10(1H, d), 5.39–5.28(2H, m), 4.21–4.15(2H, m), 4.09–4.03 (2H, m), 3.92–3.86(2H, m), 3.83–3.76(2H, m), 3.65(2H, s), 2.05(3H, s), 2.04–1.92(4H, m) |

The formulation examples of the compound of the present invention will now be shown hereinbelow. By the terms "part" and "%" are meant "part by weight" and "% by weight," respectively.

Formulation Example 1: Wettable powder

Forty parts of a compound of the present invention shown in Table 1, 20 parts of Carplex #80 (as registered trade mark; manufactured by Shionogi & Co., Ltd.), 35 parts of N,N Kaolin Clay (as registered trade mark; manufactured by Tuchiya Kaolin Co., Ltd.), and 5 parts of a higher alcohol sulfate surfactant sorpol 8070 (as registered trade mark; manufactured by TOHO CHEMICAL INDUSTRY COMPANY, LIMITED) were compounded together, and subsequently mixed together and ground homogeneously, to obtain a wettable powder containing the active ingredient at 40%.

Formulation Example 2: Emulsifiable concentrate

Twenty parts of a compound of the present invention shown in Table 1 were dissolved in a mixture solvent composed of 35 parts of xylene and 30 parts dimethylformamide, to which was then added 15 parts of a polyoxyethylene surfactant Sorpol 3005X (as registered trade mark; manufactured by TOHO CHEMICAL INDUSTRY COMPANY, LIMITED), to obtain an emulsifiable concentration containing the active ingredient at 20%.

Formulation Example 3: Flowable

Thirty parts of a compound of the present invention shown in Table 1 was thoroughly mixed and dispersed in preliminarily mixed 8 parts of ethylene glycol, 5 parts of Sorpol AC 3020 (as registered trade mark; manufactured by TOHO CHEMICAL INDUSTRY COMPANY, LIMITED), 0.1 part of xanthan gum and 56.9 parts of water, and the resulting slurry mixture was subsequently wet ground with a Dynomill (as registered trade mark; manufactured by Shinmaru Enterprises Corporation), to obtain a stable flowable containing the active ingredient at 30%.

Formulation Example 4: Granule

One part of a compound of the present invention shown in Table 1, 43 parts of clay (manufactured by Nippon Talc Kabushiki Kaisha), 55 parts of bentonite (manufactured by Hojun Yoko Kabushiki Kaisha), and one part of a succinate surfactant Airroll CT-1 (as registered trade mark; manufactured by TOHO CHEMICAL INDUSTRY COMPANY, LIMITED) were blended together, and mixed together and ground, followed by addition of water. The resulting mixture was then kneaded.

By using an extrusion granulating machine, the resulting mixture was extruded from holes each of a diameter of 0.6 mm, and dried at 60 °C. for 2 hours, which was then cut at a length of 1-2 mm, to obtain a granule containing the active ingredient at 1%.

The test examples of the compound of the present invention will now be shown below.

The Comparative Compounds (A) to (E) in the Test Examples herein show the following compounds. Comparative Compound (A)

Acifluorfen-sodium

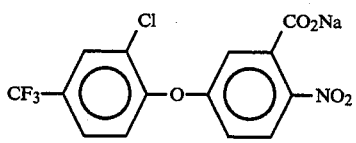

Comparative Compound (B)

9-(4-Chloro-2-fluoro-5-(isopropyloxy)phenylimino)-8-thia-1,6diazabicyclo[4.3.0]nonan-7-one (disclosed in Japanese Patent Laid-open No. 91/1987)

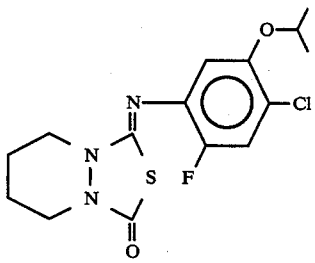

Comparative Compound (C)

9-(5-(n-Butoxycarbonylmethylthio )-4-chloro-2-fluorophenylimino)-8-thia-1,6-diazabicyclo[4.3.0]nonan-7-one (disclosed in European Patent Publication No. 273417)

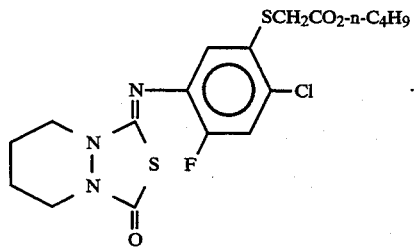

Comparative Compound (D)

9-(4-Chloro-5( cyclopentyloxycarbonylmethylthio ) -2-fluorophenylimino 8-thia-1,6-diazabicyclo[4.3.0]nonan-7-on (disclosed in European Patent Publication No. 273417)

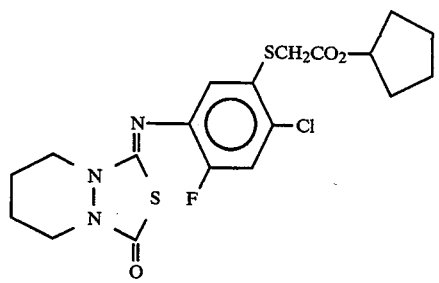

Comparative Compound (E)

9-(4-Chloro-2-fluoro-5( tetrahydrofuran-2-ylmethoxycarbonylmethylthio)phenylimino)-8-thia-1,6-diazabicyclo[4.3.0 ]nonan-7-one (disclosed in Japanese Patent Laid-open No. 199978/1991)

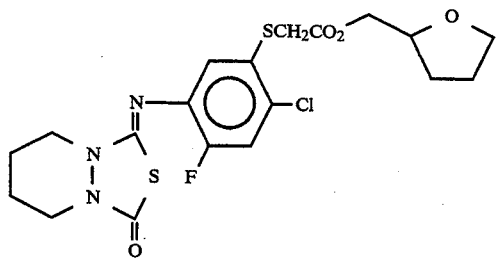

Test Example 1: Foliar application test

A small, styrol foaming-made pot of an area of 110 cm$^2$ was filled with andosol of volcanic ash, followed by application of a fertilizer. Then, each seed of *Amaranthus viridis, Polygonum lapathifolium, Abutilon theophrasti, Xanthium strumarium, Galium aparine, Viola tricolor*, corn, wheat and soybean was seeded in an individual pot.

The culture control was continued in a greenhouse. Dilution of the wettable powder containing as the active ingredient the compound of the present invention obtained by the Formulation Example 1, and the wettable powder individually containing as the effective ingredients the Comparative Compounds (A), (B), and (C) obtained in the same fashion as in the Formulation Example 1 were done separately with water so that the active ingredient contents might be 250,125, 63 and 32 g/ha. An amount of 500 liters as the application solution volume per 1 ha was applied to the foliage parts with small power pressure sprayers when *Amaranthus viridis* seedlings reached 3.5 leaf stage; *Polygonum lapathifolium*, 3 leaf stage; *Abutilon theophrasti* seedlings, 3 leaf stage; *Xanthium strumarium* seedlings, 3 leaf stage; *Galium aparine* seedlings, 2 node-leaf stage; *Viola tricolor* seedlings, 3 leaf stage; corn seedlings, 3.5 leaf stage; wheat seedlings, 2.5 leaf stage; and soybean seedlings, 1.5 leaf stage.

Subsequently, the culture control was continued in the greenhouse, and on day 21 after the chemical application, observation was done about herbicidal effect and crop injury.

The results are shown in Table 3.

The assessment of herbicidal effect was done as follows:

The value;

$$\left(1 - \frac{\text{fresh weight of weed above-ground part in a treatment}}{\text{fresh weight of weed above-ground part in an untreatment}}\right) \times 100 = Y\%$$

was determined, which was then represented as the herbicidal effect coefficient according to the following criteria:

| Herbicidal effect coefficient | Y (%) |
|---|---|
| 0 | 0–5 |
| 1 | 6–30 |
| 2 | 31–50 |
| 3 | 51–70 |
| 4 | 71–90 |
| 5 | 90–100 |

The assessment of crop injury was done as follows:

The value;

$$\left(1 - \frac{\text{fresh weight of crop above-ground part in a treatment}}{\text{fresh weight of crop above-ground part in an untreatment}}\right) \times 100 = Y\%$$

was determined, which was then represented as the crop injury coefficient according to the following criteria:

| Crop injury coefficient | Y (%) |
|---|---|
| 0 | 0–5 |
| 1 | 6–10 |
| 2 | 11–20 |
| 3 | 21–40 |
| 4 | 41–60 |
| 5 | 61–100 |

TABLE 3

| Compound No. | Rate of application g/ha | Herbicidal effect | | | | | | Crop injury | | |
|---|---|---|---|---|---|---|---|---|---|---|
| | | *Amaranthus viridis* | *Polygonum lapathifolium* | *Abutilon theophrasti* | *Xanthium strumarium* | *Galium aparine* | *Viola tricolor* | corn | wheat | soybean |
| 2 | 250 | 5 | 5 | 5 | 5 | 5 | 5 | 0 | 0 | 1 |
| | 125 | 5 | 4 | 5 | 3 | 5 | 5 | 0 | 0 | 0 |
| 4 | 250 | 5 | 5 | 5 | 5 | 5 | 5 | 0 | 0 | 0 |
| | 125 | 5 | 5 | 5 | 4 | 5 | 5 | 0 | 0 | 0 |
| 5 | 250 | 5 | 5 | 5 | 5 | 5 | 5 | 0 | 0 | 0 |
| | 125 | 5 | 5 | 5 | 3 | 4 | 5 | 0 | 0 | 0 |
| 6 | 250 | 5 | 5 | 5 | 5 | 5 | 5 | 0 | 0 | 0 |
| | 125 | 5 | 5 | 4 | 4 | 5 | 5 | 0 | 0 | 0 |
| 7 | 63 | 5 | 5 | 5 | 5 | 5 | 5 | 0 | 0 | 1 |
| | 32 | 5 | 5 | 5 | 5 | 5 | 5 | 0 | 0 | 0 |
| 8 | 63 | 5 | 5 | 5 | 5 | 5 | 5 | 0 | 0 | 0 |
| | 32 | 5 | 5 | 5 | 5 | 5 | 5 | 0 | 0 | 0 |
| 9 | 63 | 5 | 5 | 5 | 5 | 5 | 5 | 0 | 1 | 1 |
| | 32 | 5 | 5 | 5 | 5 | 5 | 5 | 0 | 0 | 0 |
| 10 | 63 | 5 | 5 | 5 | 5 | 5 | 5 | 1 | 1 | 1 |
| | 32 | 5 | 5 | 5 | 5 | 5 | 5 | 0 | 0 | 1 |
| 11 | 125 | 5 | 5 | 5 | 5 | 5 | 5 | 0 | 1 | 1 |
| | 63 | 5 | 5 | 5 | 3 | 4 | 5 | 0 | 0 | 0 |
| 12 | 125 | 5 | 5 | 5 | 5 | 5 | 5 | 0 | 0 | 0 |
| | 63 | 5 | 4 | 5 | 3 | 4 | 4 | 0 | 0 | 0 |
| 13 | 125 | 5 | 5 | 5 | 5 | 5 | 5 | 0 | 0 | 1 |
| | 63 | 5 | 5 | 5 | 3 | 4 | 5 | 0 | 0 | 0 |
| 14 | 125 | 5 | 5 | 5 | 5 | 5 | 5 | 0 | 0 | 0 |
| | 63 | 5 | 4 | 5 | 4 | 4 | 5 | 0 | 0 | 0 |
| 18 | 125 | 5 | 5 | 5 | 5 | 5 | 5 | 0 | 0 | 1 |
| | 63 | 5 | 5 | 5 | 4 | 5 | 5 | 0 | 0 | 0 |
| 20 | 125 | 5 | 5 | 5 | 5 | 5 | 5 | 0 | 1 | 1 |
| | 63 | 5 | 5 | 5 | 4 | 5 | 5 | 0 | 0 | 0 |
| 21 | 125 | 5 | 5 | 5 | 5 | 5 | 5 | 0 | 0 | 1 |
| | 63 | 5 | 5 | 5 | 4 | 5 | 5 | 0 | 0 | 0 |
| 22 | 63 | 5 | 5 | 5 | 5 | 5 | 5 | 0 | 1 | 2 |
| | 32 | 5 | 5 | 5 | 5 | 5 | 5 | 0 | 0 | 0 |
| 23 | 63 | 5 | 5 | 5 | 5 | 5 | 5 | 0 | 0 | 1 |
| | 32 | 5 | 5 | 5 | 5 | 5 | 5 | 0 | 0 | 0 |
| 25 | 63 | 5 | 5 | 5 | 5 | 5 | 5 | 0 | 1 | 1 |
| | 32 | 5 | 5 | 5 | 5 | 5 | 5 | 0 | 0 | 0 |
| 26 | 63 | 5 | 5 | 5 | 5 | 5 | 5 | 0 | 0 | 1 |
| | 32 | 5 | 5 | 5 | 5 | 5 | 5 | 0 | 0 | 0 |
| 27 | 63 | 5 | 5 | 5 | 5 | 5 | 5 | 0 | 0 | 1 |
| | 32 | 5 | 5 | 5 | 5 | 5 | 5 | 0 | 0 | 0 |
| 28 | 63 | 5 | 5 | 5 | 5 | 5 | 5 | 0 | 0 | 1 |
| | 32 | 5 | 5 | 5 | 5 | 5 | 5 | 0 | 0 | 0 |
| 29 | 63 | 5 | 5 | 5 | 5 | 5 | 5 | 0 | 0 | 1 |
| | 32 | 5 | 5 | 5 | 5 | 5 | 5 | 0 | 0 | 0 |
| 30 | 63 | 5 | 5 | 5 | 5 | 5 | 5 | 0 | 0 | 1 |
| | 32 | 5 | 5 | 5 | 5 | 5 | 5 | 0 | 0 | 0 |
| 31 | 63 | 5 | 5 | 5 | 5 | 5 | 5 | 0 | 0 | 1 |
| | 32 | 5 | 5 | 5 | 5 | 5 | 5 | 0 | 0 | 0 |
| 33 | 63 | 5 | 5 | 5 | 5 | 5 | 5 | 0 | 0 | 0 |
| | 32 | 5 | 5 | 5 | 5 | 5 | 5 | 0 | 0 | 0 |
| 34 | 63 | 5 | 5 | 5 | 5 | 5 | 5 | 0 | 1 | 1 |
| | 32 | 5 | 5 | 5 | 5 | 5 | 5 | 0 | 0 | 0 |

TABLE 3-continued

| Compound No. | Rate of application g/ha | Herbicidal effect ||||||  Crop injury |||
|---|---|---|---|---|---|---|---|---|---|---|
| | | Amaranthus viridis | Polygonum lapathifolium | Abutilon theophrasti | Xanthium strumarium | Galium aparine | Viola tricolor | corn | wheat | soybean |
| 35 | 63 | 5 | 5 | 5 | 5 | 5 | 5 | 0 | 0 | 1 |
| | 32 | 5 | 5 | 5 | 5 | 5 | 5 | 0 | 0 | 0 |
| 36 | 63 | 5 | 5 | 5 | 5 | 5 | 5 | 0 | 0 | 1 |
| | 32 | 5 | 5 | 5 | 5 | 5 | 5 | 0 | 0 | 0 |
| 37 | 63 | 5 | 5 | 5 | 5 | 5 | 5 | 0 | 0 | 1 |
| | 32 | 5 | 5 | 5 | 5 | 5 | 5 | 0 | 0 | 0 |
| 38 | 63 | 5 | 5 | 5 | 5 | 5 | 5 | 0 | 1 | 1 |
| | 32 | 5 | 5 | 5 | 5 | 5 | 5 | 0 | 0 | 0 |
| 39 | 63 | 5 | 5 | 5 | 5 | 5 | 5 | 1 | 1 | 0 |
| | 32 | 5 | 5 | 5 | 5 | 5 | 5 | 0 | 0 | 0 |
| 40 | 63 | 5 | 5 | 5 | 5 | 5 | 5 | 0 | 1 | 1 |
| | 32 | 5 | 5 | 5 | 5 | 5 | 5 | 0 | 0 | 0 |
| 42 | 125 | 5 | 5 | 5 | 5 | 5 | 5 | 0 | 0 | 1 |
| | 63 | 5 | 5 | 5 | 4 | 5 | 5 | 0 | 0 | 0 |
| 43 | 125 | 5 | 5 | 5 | 5 | 5 | 5 | 0 | 0 | 0 |
| | 63 | 5 | 5 | 5 | 5 | 5 | 5 | 0 | 0 | 0 |
| Comparative compound (A) | 250 | 5 | 5 | 3 | 4 | 3 | 4 | 1 | 2 | 1 |
| | 125 | 2 | 3 | 2 | 2 | 1 | 1 | 0 | 0 | 0 |
| Comparative compound (B) | 125 | 5 | 5 | 5 | 4 | 5 | 5 | 3 | 3 | 4 |
| | 63 | 5 | 5 | 5 | 3 | 5 | 5 | 2 | 2 | 3 |
| Comparative compound (C) | 125 | 5 | 5 | 5 | 5 | 5 | 5 | 2 | 2 | 2 |
| | 63 | 5 | 5 | 5 | 5 | 5 | 5 | 1 | 2 | 1 |
| Untreated | — | 0 | 0 | 0 | 0 | 0 | 0 | 0 | 0 | 0 |

Test Example 2: Soil application test

A resin tray of an area of 600 cm2 was filled with andosol of volcanic ash, followed by application of a fertilizer and subsequent sowing of each crop seed of corn, wheat and soybean, followed by soil covering of about 2 cm thickness. Furthermore, on the soil surface was placed uniformly the soil mixed with each weed seed of *Chenopodium album, Polygonum lapathifolium, Brassica juncea,* and *Viola tricolor*. Dilution with water of the wettable powder containing as the active ingredient the compound of the present invention obtained by the Formulation Example 1 or the wettable powder individually containing as the active ingredients the Comparative Compounds (A), (B), and (C) shown in the Test Example 1 which were obtained in the same fashion as in the Formulation Example 1, was done. Subsequently, the diluted agents were applied to the soil surface uniformly with small power pressure sprayers at such amounts that the active ingredient contents might be 2.5, and 1.25 kg/ha, individually.

The culture control was then continued in the greenhouse, and on day 21 after the chemical application, observation was done about the herbicidal effect and the crop injury.

The results are shown in Table 4.

The assessment of the herbicidal effect and the crop injury was represented following the criteria of the Test Example 1.

TABLE 4

| Compound No. | Rate of application kg/ha | Herbicidal effect |||| Crop injury |||
|---|---|---|---|---|---|---|---|---|
| | | Chenopodium album | Polygonum lapathifolium | Brassica juncea | Viola tricolor | corn | wheat | soybean |
| 7 | 2.5 | 5 | 5 | 5 | 5 | 0 | 0 | 0 |
| | 1.25 | 5 | 4 | 4 | 5 | 0 | 0 | 0 |
| 8 | 2.5 | 5 | 5 | 5 | 5 | 0 | 0 | 1 |
| | 1.25 | 5 | 4 | 5 | 5 | 0 | 0 | 0 |
| 10 | 2.5 | 5 | 5 | 5 | 5 | 0 | 2 | 1 |
| | 1.25 | 5 | 5 | 5 | 5 | 0 | 0 | 0 |
| 14 | 2.5 | 5 | 5 | 5 | 5 | 0 | 1 | 1 |
| | 1.25 | 5 | 5 | 4 | 5 | 0 | 0 | 0 |
| 21 | 2.5 | 5 | 5 | 5 | 5 | 0 | 0 | 0 |
| | 1.25 | 5 | 5 | 4 | 4 | 0 | 0 | 0 |
| 23 | 2.5 | 5 | 5 | 5 | 5 | 0 | 0 | 0 |
| | 1.25 | 5 | 4 | 3 | 5 | 0 | 0 | 0 |
| 26 | 2.5 | 5 | 5 | 5 | 5 | 0 | 0 | 0 |
| | 1.25 | 5 | 5 | 4 | 5 | 0 | 0 | 0 |
| 38 | 2.5 | 5 | 5 | 5 | 5 | 0 | 0 | 1 |
| | 1.25 | 5 | 5 | 5 | 5 | 0 | 0 | 0 |
| Comparative compound (A) | 2.5 | 5 | 4 | 4 | 5 | 0 | 3 | 2 |
| | 1.25 | 4 | 4 | 2 | 3 | 0 | 0 | 0 |
| Comparative compound (B) | 2.5 | 5 | 5 | 5 | 5 | 1 | 3 | 2 |
| | 1.25 | 5 | 5 | 4 | 5 | 0 | 1 | 0 |
| Comparative compound (C) | 2.5 | 5 | 5 | 5 | 5 | 0 | 2 | 2 |
| | 1.25 | 5 | 5 | 4 | 5 | 0 | 1 | 1 |

TABLE 4-continued

| Compound No. | Rate of application kg/ha | Herbicidal effect | | | | Crop injury | | |
|---|---|---|---|---|---|---|---|---|
| | | Chenopodium album | Polygonum lapathifolium | Brassica juncea | Viola tricolor | corn | wheat | soybean |
| Untreated | — | 0 | 0 | 0 | 0 | 0 | 0 | 0 |

Test Example 3: Submerged application test

A resin tray of an area of 400 cm² was filled with rice-field alluvium soil, followed by application of a fertilizer and subsequent addition of an appropriate amount of water for plowing. Inside a 0.5-cm layer from the soil surface was mixed each weed seed of *Echinochloa crus-galli, Monochoria vaginalis,* and *Scirpus juncoides.* On the soil surface were planted 4 tubers of *Cyperus serotinus* per tray.

Furthermore, 2 plants (three pieces/plant) of paddy-rice seedlings of 2.3 leaf stage (species: Akinishiki) were transplanted in each of the trays, followed by water injection, to keep a water filling depth of about 3.5 cm.

On day 5 after the weed seeding or the transplantation of the paddy-rice seedlings, the granules containing as the active ingredient the compound of the present invention obtained by the Formulation Example 4 or the granules containing as the active ingredients the Comparative Compounds (A), (B), and (C) shown in the Test Example 1 which were obtained in the same fashion as in the Formulation Example 4, were subjected to falling application to the water-filled surface at such amounts that the active ingredient contents might be 500, 250, and 125 g per 1 ha, individually.

The culture control was then continued in the greenhouse, and on day 21 after the chemical application, observation was done about the herbicidal effect and the crop injury on the transplanted paddy-rice plants.

The results are shown in Table 5.

The assessment of herbicidal effect and crop injury on the transplanted paddy-rice plants was represented following the criteria of the Test Example 1.

TABLE 5

| Compound No. | Rate of application g/ha | Herbicidal effect | | | | Crop injury transplanted paddy-rice plant |
|---|---|---|---|---|---|---|
| | | Echinochloa crus-galli | Monochoria vaginalis | Scirpus juncides | Cyperus serotinus | |
| 1 | 500 | 5 | 5 | 5 | 5 | 0 |
| | 250 | 3 | 5 | 4 | 4 | 0 |
| 2 | 500 | 5 | 5 | 5 | 5 | 0 |
| | 250 | 4 | 5 | 4 | 5 | 0 |
| 3 | 500 | 5 | 5 | 5 | 5 | 0 |
| | 250 | 4 | 5 | 4 | 5 | 0 |
| 7 | 250 | 5 | 5 | 5 | 5 | 1 |
| | 125 | 5 | 5 | 5 | 5 | 0 |
| 8 | 250 | 5 | 5 | 5 | 5 | 1 |
| | 125 | 4 | 5 | 5 | 5 | 0 |
| 9 | 250 | 5 | 5 | 5 | 5 | 1 |
| | 125 | 5 | 5 | 5 | 5 | 0 |
| 10 | 250 | 5 | 5 | 5 | 5 | 2 |
| | 125 | 5 | 5 | 5 | 5 | 0 |
| 16 | 500 | 5 | 5 | 5 | 5 | 0 |
| | 250 | 2 | 4 | 4 | 5 | 0 |
| 17 | 500 | 5 | 5 | 5 | 5 | 1 |
| | 250 | 4 | 5 | 4 | 5 | 0 |
| 22 | 250 | 5 | 5 | 5 | 5 | 1 |
| | 125 | 5 | 5 | 5 | 5 | 0 |
| 23 | 250 | 5 | 5 | 5 | 5 | 1 |
| | 125 | 5 | 5 | 5 | 5 | 0 |
| 26 | 250 | 5 | 5 | 5 | 5 | 1 |
| | 125 | 5 | 5 | 5 | 5 | 0 |
| 27 | 250 | 5 | 5 | 5 | 5 | 0 |
| | 125 | 4 | 5 | 4 | 5 | 0 |
| 33 | 250 | 5 | 5 | 5 | 5 | 0 |
| | 125 | 3 | 5 | 5 | 5 | 0 |
| 42 | 500 | 5 | 5 | 5 | 5 | 0 |
| | 250 | 4 | 5 | 4 | 5 | 0 |
| 43 | 500 | 5 | 5 | 5 | 5 | 1 |
| | 250 | 5 | 5 | 5 | 5 | 0 |
| Comparative compound (A) | 250 | 4 | 5 | 3 | 5 | 1 |
| | 125 | 3 | 3 | 0 | 3 | 0 |
| Comparative compound (B) | 250 | 5 | 5 | 5 | 5 | 4 |
| | 125 | 5 | 5 | 4 | 5 | 3 |
| Comparative compound (C) | 250 | 5 | 5 | 5 | 5 | 4 |
| | 125 | 5 | 5 | 5 | 5 | 2 |
| Untreated | — | 0 | 0 | 0 | 0 | 0 |

Test Example 4: Foliar application test (herbicidal effect)

An unglazed pottery of an area of 180 cm² was filled with andosol of volcanic ash, followed by application of a fertilizer, and then each weed seed of *Abutilon theophrasti*, *Xanthium strumarium*, and *Ipomoea purpurea* was seeded.

The culture control was continued in a greenhouse. The compound No.26 of the present invention and the Comparative Compounds (C), (D) and (E) were individually dissolved in acetone and a surfactant (Tween 20) to obtain 10% simple emulsions, which were then diluted with water so that the active ingredient contents might be 50, 25, 12.5, 6.3, and 3.1 g/ha, individually. The resulting solutions were applied to the foliage part of each weed with a small power pressure sprayer at an amount of 250 liters for application to 1 ha, when *Abutilon theophrasti* seedlings reached 4 to 4.5 leaf stage; *Xanthium strumarium* seedlings, 4.5 to 5 leaf stage; *Ipomoea purpurea* seedlings, 3 to 3.5 leaf stage.

The culture control was thereafter continued in the greenhouse, to observe the herbicidal effect on day 28 after the chemical application.

The results are shown in Table 6.

The herbicidal effect was evaluated visually, and represented on the basis of the following criteria.

| | |
|---|---|
| 0 | No effect |
| 25 | 25% weed control |
| 50 | 50% weed control |
| 75 | 75% weed control |
| 100 | completely killed | ually. The resulting solutions were applied to the foliage part of each crop with a small power pressure sprayer at an amount of 250 liters for application to 1 ha, when the growth leaf stage of the subjective crops, namely corn and soybean, reached 3.8 to 4 leaf stage and 1.3 to 1.5 trifoliolate leaf stage, respectively.

The culture control was thereafter continued in the greenhouse, to observe the crop injury on day 7 and 14 after the chemical application.

The results are shown in Table 7.

The crop injury was evaluated visually, and represented on the basis of the following criteria.

| | |
|---|---|
| 0 | No crop injury |
| 25 | 25% crop injury |
| 50 | 50% crop injury |
| 75 | 75% crop injury |
| 100 | Complete crop destruction |

TABLE 7

| Compound | Rate of application g/ha | Corn injury | | Soybean injury | |
|---|---|---|---|---|---|
| NO. 26 | 400 | 10[1] | 5[2] | 23[3] | 20[4] |
| | 200 | 10 | 0 | 17 | 13 |
| | 100 | 0 | 0 | 3 | 0 |
| | 50 | 0 | 0 | 0 | 0 |
| Comparative compound | 400 | 55 | 40 | 47 | 43 |
| | 200 | 35 | 30 | 43 | 37 |
| (C) | 100 | 15 | 10 | 23 | 20 |
| | 50 | 5 | 5 | 13 | 7 |
| Comparative compound | 400 | 50 | 40 | 40 | 33 |
| | 200 | 35 | 25 | 33 | 27 |
| (D) | 100 | 20 | 15 | 17 | 13 |
| | 50 | 10 | 5 | 3 | 3 |
| Comparative compound | 400 | 20 | 15 | 40 | 37 |
| | 200 | 10 | 5 | 33 | 27 |
| (E) | 100 | 5 | 5 | 17 | 10 |
| | 50 | 0 | 0 | 7 | 3 |

TABLE 6

| Compound | Rate of application g/ha | Herbicidal effect | | | Average value of herbicidal effect on three weed species |
|---|---|---|---|---|---|
| | | *Abutilon theoparasti* | *Xanthium strumarium* | *Ipomoea purpurea* | |
| No. 26 | 50 | 100[1] | 100 | 100 | 100 |
| | 25 | 100 | 100 | 100 | 100 |
| | 12.5 | 100 | 80 | 100 | 93 |
| | 6.3 | 100 | 20 | 90 | 70 |
| | 3.1 | 100 | 0 | 80 | 60 |
| Comparative compound (C) | 50 | 100 | 100 | 100 | 100 |
| | 25 | 100 | 100 | 100 | 100 |
| | 12.5 | 100 | 100 | 100 | 100 |
| | 6.3 | 100 | 70 | 80 | 83 |
| | 3.1 | 100 | 30 | 80 | 70 |
| Comparative compound (D) | 50 | 100 | 100 | 100 | 100 |
| | 25 | 100 | 100 | 100 | 100 |
| | 12.5 | 100 | 80 | 100 | 93 |
| | 6.3 | 100 | 20 | 90 | 70 |
| | 3.1 | 100 | 5 | 70 | 58 |
| Comparative compound (E) | 50 | 100 | 100 | 100 | 100 |
| | 25 | 100 | 100 | 100 | 100 |
| | 12.5 | 100 | 90 | 90 | 93 |
| | 6.3 | 100 | 10 | 75 | 63 |
| | 3.1 | 100 | 0 | 60 | 53 |
| Untreated | — | 0 | 0 | 0 | 0 |

Note
[1] 2 replications average value

Test Example 5: Foliar application test (Crop injury)

An unglazed pottery of an area of 180 cm² was filled with andosol of volcanic ash, followed by application of a fertilizer, and then each seed of corn (Pioneer species S115) and soybean (Williams 82) was seeded per pot.

The culture control was continued in a greenhouse, and the compound No. 26 of the present invention and the Comparative Compounds (C), (D) and (E) were individually dissolved in acetone and an activator (Tween 20) to obtain 10% simple emulsions, which were then diluted with water so that the active ingredient contents might be 400, 200, 100, and 50 g/ha, individ-

TABLE 7-continued

| Compound | Rate of application g/ha | Corn injury | | Soybean injury | |
|---|---|---|---|---|---|
| Untreated | — | 0 | 0 | 0 | 0 |

Note:
[1] Initial crop injury (the result of the observation on day 7 after chemical application; 2-replications average value)
[2] Final crop injury (the result of the observation on day 14 after chemical application; 2-replications average value)
[3] Initial crop injury (the result of the observation on day 7 after chemical application; 3-replications average value)
[4] Final crop injury (the result of the observation on day 14 after chemical application; 3-replications average value)

Selectivity of the compound of the present invention on corn and soybean

From the Test Example 4, a chemical dose of each compound controlling 90% of 3 species of weeds ($ED_{90}$) was calculated as an indicator for representing the herbicidal activity. From the Test Example 5, a chemical dose of each compound inhibiting 20% of the growth of corn or soybean ($ID_{20}$) was calculated as an indicator for representing the crop injury. By using these values, $ID_{20}/ED_{90}$ was calculated as an indicator representing the selectivity between the weeds and crops.

The results are shown in Table 8.

TABLE 8

| Compound | Herbicidal effect $ED_{90}$ (g/ha) | Crop injury*[1] $ID_{20}$ (g/ha) | | Selectivity ($ID_{20}/ED_{90}$) | |
|---|---|---|---|---|---|
| | | corn | soybean | corn | soybean |
| No. 26 | 12 | >400 | 300 | >33 | 25 |
| Comparative compound (C) | 9 | 130 | 80 | 14 | 9 |
| Comparative compound (D) | 12 | 100 | 150 | 8 | 13 |
| Comparative compound (E) | 13 | 370 | 130 | 28 | 10 |

Note
[1] $ID_{20}$ at initial crop injury

As shown in the Test Examples described above, the compounds of the present invention not only have strong herbicidal activity, but also are far more excellent than the known similar compounds from the respect of safety on crops. Thus, the compounds are useful as a herbicides.

What is claimed is:

1. A tetrahydrofuran compound of the formula

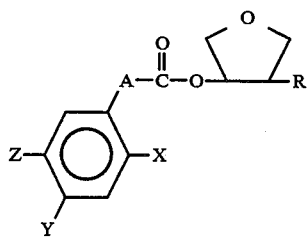

wherein A represents a direct bond or a group represented by —B—CHR$^1$— wherein B represents oxygen atom, sulfur atom or imino and R$^1$ represents hydrogen atom or alkyl of C$_1$-C$_4$;

R represents hydrogen, halogen, hydroxyl, alkoxy of C$_1$-C$_4$, benzyloxy, alkylsulfonyloxy of C$_1$-C$_3$ or a group represented by —O—COR$^2$ wherein R$^2$ represents alkyl of C$_1$-C$_5$, haloalkyl of C$_1$-C$_3$, alkenyl of C$_2$-C$_5$, cycloalkyl of C$_3$-C$_6$, phenyl, benzyl, alkoxy of C$_1$-C$_4$, alkylamino of C$_1$-C$_4$ or dialkylamino of C$_2$-C$_6$;

X represents halogen;

Y represents hydrogen or halogen; and

Z is a group represented by

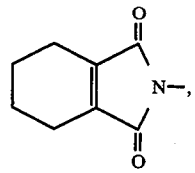

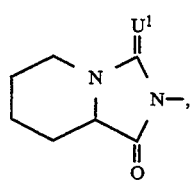

or

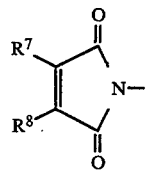

wherein U$^1$ represents oxygen or sulfur and R$^7$ and R$^8$ independently represent alkyl of C$_1$-C$_4$.

2. A tetrahydrofuran compound according to claim 1, wherein R represents hydrogen, hydroxyl, benzyloxy, alkylsulfonyloxy of C$_1$-C$_3$ or a group represented by —O—COR$^2$ wherein R$^2$ represents alkyl of C$_1$-C$_5$, haloalkyl of C$_1$-C$_3$, alkenyl of C$_2$-C$_5$, cycloalkyl of C$_3$-C$_6$, phenyl, or alkoxy of C$_1$C$_4$; and Z is a group represented by

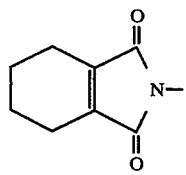

or

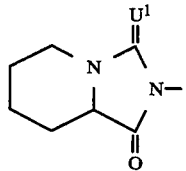

wherein U$^1$ represents oxygen or sulfur.

3. A tetrahydrofuran compound according to claim 2, wherein R represents hydrogen, hydroxyl, alkylsulfonyloxy of C$_1$-C$_3$ or a group represented by —O—COR$^2$ wherein R$^2$ represents alkyl of C$_1$-C$_5$, alkenyl of C$_2$-C$_5$, cycloalkyl of C$_3$-C$_6$, phenyl, or alkoxy of C$_1$–C$_4$.

4. A herbicidal composition which comprises a herbicidally effective amount of a tetrahydrofuran compound according to claim 1 and a suitable carrier therefor.

5. A method for suppressing weed growth, comprising treating the plants or the growth soil thereof with a herbicidally effective amount of a tetrahydrofuran compound according to claim 1.

* * * * *

UNITED STATES PATENT AND TRADEMARK OFFICE
CERTIFICATE OF CORRECTION

PATENT NO. : 5,405,828
DATED : April 11, 1995
INVENTOR(S) : BUNJI NATSUME, NOBUO KYOMURA, SEIICHI SUZUKI, YOJI TAKAHASHI and TETSUO JIKIHARA It is certified that error appears in the above-indentified patent and that said Letters Patent is hereby corrected as shown below:

On the cover page of the patent, "[75] Inventors:", correct the names of the inventors to read:

—BUNJI NATSUME, NOBUO KYOMURA, SEIICHI SUZUKI,

Tokyo; YOJI TAKAHASHI, Tokyo; TETSUO JIKIHARA,

Tokyo, all of Japan—.

Column 40, line 43, change "$C_1C_4$" to read —$C_1$-$C_4$—.

Signed and Sealed this

Twenty-sixth Day of September, 1995

Attest:

BRUCE LEHMAN

Attesting Officer      Commissioner of Patents and Trademarks